United States Patent [19]

Ishihara et al.

[11] Patent Number: 5,598,842
[45] Date of Patent: Feb. 4, 1997

[54] NON-INVASIVE BLOOD ANALYZER AND METHOD USING THE SAME

[75] Inventors: Ken Ishihara, Takarazuka; Hiroshi Yamamoto, Kobe; Mitsuru Watanabe, Kobe; Kaoru Asano, Kobe; Akio Suzuki, Akashi; Yasunori Maekawa, Miki, all of Japan

[73] Assignee: Toa Medical Electronics Co., Ltd., Hyogo, Japan

[21] Appl. No.: 296,897

[22] Filed: Aug. 29, 1994

[30] Foreign Application Priority Data

Sep. 3, 1993 [JP] Japan .................................... 5-220147
Mar. 25, 1994 [JP] Japan .................................... 6-056259

[51] Int. Cl.$^6$ .................................... A61B 5/00; A61B 1/04
[52] U.S. Cl. ............................................. 128/637; 356/39
[58] Field of Search .................................... 128/633, 632, 128/667, 637; 356/40, 39; 348/79, 80

[56] References Cited

U.S. PATENT DOCUMENTS

| | | | |
|---|---|---|---|
| 4,453,266 | 6/1984 | Bacus | 382/6 |
| 4,974,094 | 11/1990 | Morito | 358/225 |
| 4,998,533 | 3/1991 | Winkelman . | |
| 5,080,098 | 1/1992 | Willett et al. | 128/633 |
| 5,348,003 | 9/1994 | Caro . | |

FOREIGN PATENT DOCUMENTS

| | | | |
|---|---|---|---|
| 0282210 | 9/1988 | European Pat. Off. . | |
| 3619442 | 12/1987 | Germany | 128/633 |
| 4161915 | 6/1992 | Japan . | |
| WOA8103224 | 11/1981 | WIPO . | |
| WOA8800447 | 1/1988 | WIPO . | |
| 9203965 | 3/1992 | WIPO | 128/637 |
| A9313706 | 7/1993 | WIPO . | |

OTHER PUBLICATIONS

Fagrell, B. and Ostergren, J., "Capillary Flow Measurements in Human Skin" in *Clinical Investigation of the Microcirculation*, pp. 23–33.1987.

Ieee Engineering in Medicine and Biology, vol. 13, No. 3, Jul. 1994 New York, pp. 319–325.

A. Hashizume, R. Suzuki, H. Yokouchi, H. Horiuchi, S. Yamamato, *An Algorithm of Automated RBC Classification and Its Evaluation*, Medical Electronics and Bio-Engineering, vol. 28, No. 1, Mar. 1990, pp. 25–32.

*Primary Examiner*—Angela D. Sykes
*Assistant Examiner*—Eric F. Winakur

[57] ABSTRACT

A non-invasive blood analyzer includes a light application device for applying light to a detection region of vessels contained in part of the living body, an imaging device for imaging the detection region to which light is applied, a fixing device for relatively fixing the imaging device and the part of the living body; a stabilizing device for stabilizing a focus of the imaging device with respect to the detection region; and an analyzer for analyzing the morphology and/or number of blood cells contained in the detection region by processing images captured with the imaging device, the light application device and the imaging device forming one image with a light application and capturing process during an interval of one ten thousandth to one billionth of a second.

35 Claims, 19 Drawing Sheets

NON-INVASIVE BLOOD ANALYZER AND METHOD USING THE SAME

BACKGROUND OF THE INVENTION

1. Field of the Invention

The present invention relates to an apparatus for analyzing blood in a non-invasive manner and a method using the same, and more particularly to an apparatus for analyzing blood components necessary for a hematology test by optically measuring blood flowing through blood vessels in a living body and a method using the same apparatus.

2. Description of the Related Art

The items of hematology tests such as the number of blood cells, hematocrit, hemoglobin, and corpuscular constant (mean corpuscular volume: MCV, mean corpuscular hemoglobin: MCH, and mean corpuscular hemoglobin concentration: MCHC) are extremely important for the diagnosis of diseases and the treatment thereof. Such items are most frequently used in clinical tests of patients.

Such a hematology test involves collecting blood from a living body to analyze the sample thereof with an analyzer. However, the collection of blood from the living body causes considerable pain to the living body. The above method for hematology tests is always accompanied by a fear that needles for blood collection might cause an accident due to erroneous injection when they are used for collecting blood from a different living body contracted with infectious diseases such as hepatitis and AIDS. Thus, a demand has been made for many years that an apparatus be developed that allows practitioners to perform a blood test in a non-invasive manner. When such a blood analyzer is installed beside the bed on which the living body is laid, the practitioners can monitor real-time conditions thereof on the spot without difficulty. Examples of the widely known prior art relating to such apparatus include a video microscope which applies light to a subject portion of observation on a skin surface of a living body to capture a video image thereof (static image) at a shutter speed of about one thousandth of a second and identifies discontinuous points in the blood stream which points move one by one on the static image, and an analyzer providing a video camera equipped with a high-speed shutter which captures red blood cells in the conjunctival capillary blood vessels in an eyeball (see Japanese Unexamined Patent Publication No. HEI 4-161915 published Jun. 5, 1992 and U.S. Pat. No. 4,998,533 issued to James W. Winkleman, Mar. 12, 1991).

By the way, the speed of blood flow is about five mm to ten mm per second. When images of red blood cells are captured at a shutter speed of one thousandth of a second like in the prior art, assuming that the blood flows at a rate of 10 mm per second, red blood cells move by the distance equal to the diameter thereof thereby generating a shift in the image by that diameter for consecutive shutter actuations.

Furthermore, red blood cells adjoin each other in blood vessels with a space of the diameter or less therebetween and almost all the red blood cells overlap each other in the image due to the shift in the image thereof. Consequently, the above Japanese prior art is far from allowing examiners to quantitatively measure the above test items through the morphological analysis of blood cells and the counting of the number thereof from captured images.

On the other hand, the analyzer disclosed in U.S. Pat. No. 4,998,533 captures conjunctival capillary blood vessels in an eyeball with the video camera. However, the focus of the video camera is relatively shifted at all times with respect to the captured portion of the eyeball because of a slight motion inherent in the eyeball. Thus, it is very difficult to repetitively capture the same region of the captured portion thereof with the video camera. It is impossible to mechanically stop the slight motion of the eyeball by closely contacting some object to eyeballs because the eyeball might be damaged. Furthermore, U.S. Pat. No. 4,998,533 describes counting the number of RBC and measuring HCT, MCV and MCHC, but it describes no procedure for measuring these values.

SUMMARY OF THE INVENTION

The present invention has been conceived in view of the above circumstances, and an object of the invention is to provide an apparatus and a method which can analyze blood in a non-invasive manner by imaging with good accuracy blood cells moving in blood vessels in a living body and analyzing the morphology and/or number of the blood cells from captured images.

Therefore, the present invention provides a non-invasive blood analyzer comprising: light application means for applying light to a detection region in a blood vessel contained in part of a living body; imaging means for capturing images of the detection region to which light is applied; fixing means for relatively fixing the imaging means and the part of the living body; stabilizing means for stabilizing a focus of the imaging means with respect to the detection region; and analysis means for analyzing the morphology and/or the number of blood cells contained in the detection region by processing images captured with the imaging means; the light application means and the imaging means forming one image with light application or imaging process during one ten thousandth ($10^{-4}$) to one billionth ($10^{-9}$) of a second.

The blood analyzer is characterized by analyzing blood in a living body in a non-invasive manner. Preferably, the living body is that of mammals including human bodies.

The part of the living body containing the detection region to which the light application means applies light refers to a portion having a skin that is not easily damaged by a contacting object and blood vessels below the skin, such as a lip, finger, and ear lobe. Portions like eyeballs which can be easily damaged by a contacting object are excluded from the above-mentioned part of the living body.

The detection region in the blood vessel refers to a predetermined region of blood vessels that is really present in the living body. In this particular invention, the predetermined region is referred to as a detection region. This region has such a volume that blood cells in the region can be individually differentiated.

This region may be partitioned with two parallel planes traversing orthogonally or diagonally relative to the direction of blood flow. Preferably, the distance between the parallel planes may be about 10 to 20 microns.

On the other hand, the thickness of the subject blood vessels is not limited, but capillary arteries and veins are preferable to produce a good result in reproduction of the detected state. Incidentally, blood cell information obtained in capillary arteries and veins can be translated into information on thick vessels (medium-size or large arteries and veins).

From another viewpoint, the present invention provides a non-invasive method for analyzing blood comprising the steps of: relatively fixing imaging means and part of a living body: applying light to a detection region in a blood vessel contained in the part; stabilizing a focus of the imaging means with respect to the detection region: and imaging the detection region, thereby forming an image of the detection region; and processing the formed image to perform an morphological analysis of blood cells contained in the detection region and to count the number of the blood cells; the light application step and imaging step forming one image during one ten thousandth to one billionth of a second.

BRIEF DESCRIPTION OF THE DRAWINGS

The present invention will be derailed by way of the accompanying drawings, which are not intended to limit the scope of the present invention.

DESCRIPTION OF THE PREFERRED EMBODIMENTS

Figure 1:
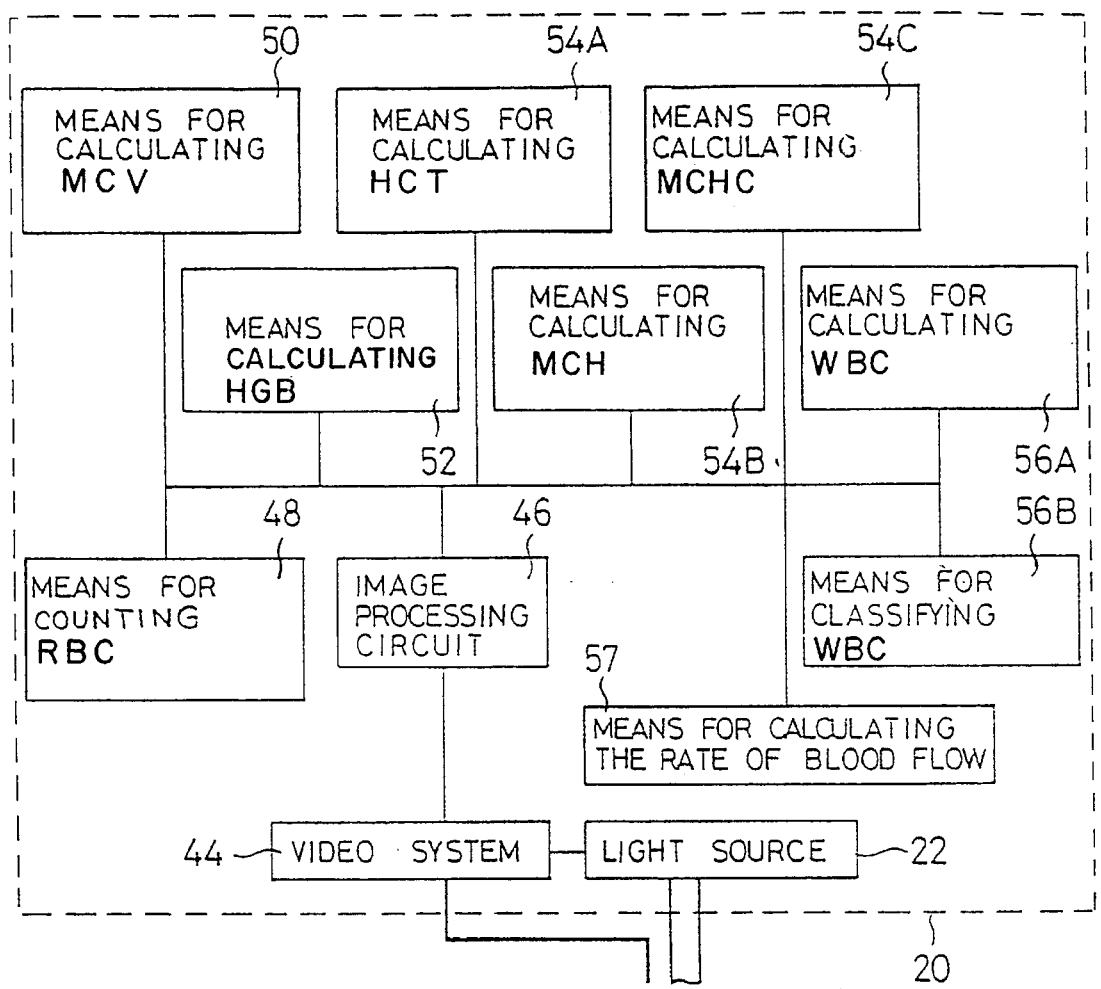
FIG. 1 is a view illustrating the structure of embodiment 1 of the present invention.

In the light application means of the present invention, either a continuous or an intermittent light source may be used; the continuous light source that continuously applies light to the detection region includes a laser, a halogen lamp or a tungsten lamp while the intermittent light source that applies light intermittently to the detection region includes a pulse laser (for example, 7000 series manufactured by Spectra-Physics Co., Ltd.) and a multi-strobe (for example, DSX series manufactured by Sugawara Laboratories, Inc., Japan). Preferably, the continuous light source may incorporate an optical shutter therein to be used as an intermittent light source. As the optical shutter, known acousticoptic modulator or electro-optic modulator can be used. Incidentally, the light application (flickering) duration in intermittent light sources of these kinds can be set to a range of one ten thousandth to one billionth of a second.

Besides, the light application means may comprise at least one of an optical fiber, various kinds of reflectors, a polarizing element, various kinds of lenses, a prism, a slit and a filter in addition to the above light source. Light emitted from the light source may be directed to the detection region by an appropriate combination of the above means. In particular, the light application means preferably comprises a polarizing means for applying light to the detection region with the polarization effect.

As the imaging means of the present invention, a general CCD image sensor for use in visible light, infrared rays and ultraviolet rays can be used. In particular, a CCD image sensor provided with an electronic shutter having a speed of one ten thousandth of a second or more is preferably used. Such CCD image sensor includes XC-73/3CE and XC-75/75CE (provided with a variable shutter having a maximum shutter speed of one five hundred thousandth of a second) both manufactured by Sony Corporation in Japan.

Furthermore, the imaging means may comprise at least one of an optical fiber, various kinds of reflectors, a polarizing element, a lens of each kind, a prism, a slit, a filter and an image intensifier so that an appropriate combination of the above devices allows the reflected light from the detection region to be introduced into the CCD image sensor. In particular, a polarizing means is preferably provided for removing unnecessary scattered light components from the detection region.

In accordance with the present invention, the light application means and the imaging means forms one image during one ten thousandth to one billionth of a second of the light application and imaging process. For example, red blood cells moving at a speed of 10 mm per sec through the vein move by a distance of one micron during one ten thousandth of a second. A shift in the image of the red blood cells captured with the device of the present invention is equal to 10% of the diameter (10 microns) of red blood cells.

The morphological analysis of blood cells in vessels and the counting of the number thereof is experimentally proved to be possible in the presence of such degree of image blur. When one image is formed in one hundred thousandth of a second, the image blur can be suppressed to one tenth thereof (1% of the diameter). When one image is formed in one millionth of a second, the image blur can be suppressed to one hundredth thereof (0.1% of the diameter). Consequently, the accuracy in the morphological analysis of blood cells and the counting thereof improves with the shortening of time required for forming one image.

However, the amount of light received by the imaging means reduces as the time for forming one image is shortened. Thus, the amount of light emitted from the light application means and/or the light sensitivity of the imaging means needs to be increased. Preferably, one image formation time ranges from one ten thousandth to one billionth of a second. More preferably, the time ranges from one fifty thousandth to one two hundred thousandth of a second. Then, in order to form one image in time ranging from one ten thousandth to one billionth of a second, preferably light application means having an intermittent light source and imaging means including CCD image sensor are combined, or light application means having a continuous light source and capturing means including a CCD image sensor with an electronic shutter are combined.

Furthermore, the light application means and the imaging means are preferably constituted to capture a plurality of images in a predetermined cycle so that the analysis means can analyze the morphology of blood cells including their color tone and/or count the number thereof based on the plurality of images.

Incidentally, the imaging means may further provide a recording means for recording captured images such as, for example, an image memory or a video tape recorder.

Generally, the number of blood cells as an item of hematology test is calculated in terms of the number per blood volume. It is necessary to know the volume of the detection region for the calculation.

Consequently, the detection region in the blood vessel to which the present invention is directed includes a three-dimensional volume region in which blood cells which exist can be optically classified. The volume (capacity) of the detection region is calculated in the following manner.

(1) The volume is calculated from an area of the captured image, a depth to which the imaging means can capture (depth of focus) and a magnification ratio thereof.

(2) Light is applied to a detection region of a predetermined volume in a blood vessel with the light application means so that the region to which light is applied is imaged.

(3) The volume of the detection region is calculated by measuring the internal diameter of the imaged blood vessel at the detection region.

In accordance with the above method (2), when a slit shaped beam of light is directed to a blood vessel in the vertical or diagonal direction relative to the blood flow with the light application means in such a manner that the blood vessel is sliced into a thin disk with the slit shaped beam of light, the imaging means images the sliced region from the direction of the cross section thereof. In this manner, the dynamic mechanism of blood cells that flows through the blood vessel can be imaged from the direction of the blood flow thereby and the volume of the detection region can be calculated from the product of the area of the cross section of the blood vessel and the slit width thereof.

In the imaging of the cross-section of the blood vessel, preferably the imaging surface of the imaging means is disposed so as to be focused on the overall surface of the cross section by the swing and tilt photography (since the swing and tilt photography is a known art, detailed description thereof is not given here).

The analysis means according to the present invention preferably provides an analog and/or digital mode image processing means selectively having functions such as each kind of filter, γ (gamma) correction, color correction, interpolation, jitter correction, color tone conversion, color balance correction, white balance and shading correction.

Furthermore, the analysis means preferably comprises means for calculating the number of red blood cells and/or white blood cells(leukocytes); means for calculating a hematocrit amount; means for calculating hemoglobin (HGB) by analyzing the intensity of reflected light from the detection region; means for calculating the mean corpuscular volume (MCV), the mean corpuscular hemoglobin (MCH) and mean corpuscular hemoglobin concentration (MCHC), based on the morphology of blood cells; means for analyzing the morphology of blood cells and classifying thus analyzed blood cells; and means for translating blood cell information obtained from arterioles and veinlets or capillary arteries and veins into blood cell information corresponding to medium-size and large arteries and veins.

The analysis means may comprise a digital signal processor (DSP), for example, TMS320C30 manufactured by Texas Instruments, Inc.

Figure 17:
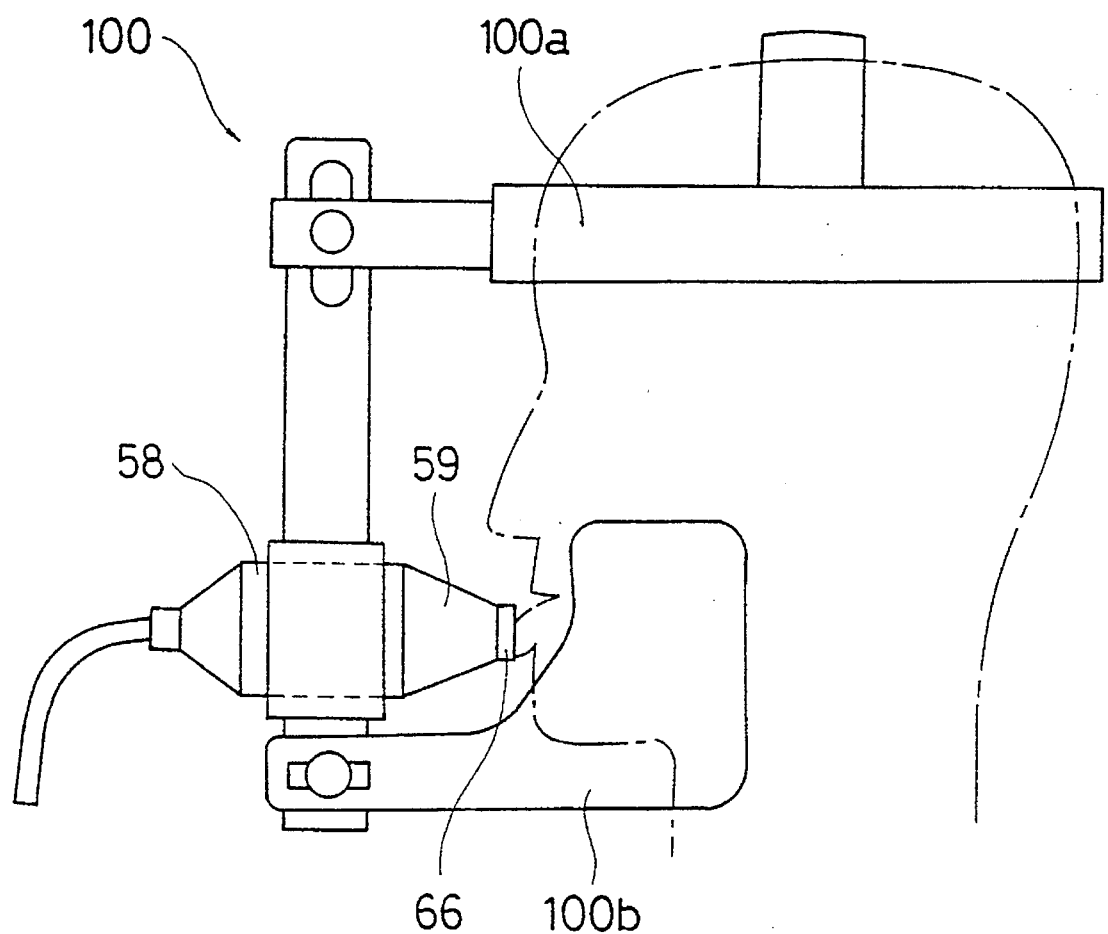
FIG. 17 is a view showing an example in which a probe is attached in an embodiment.
Figure 21:
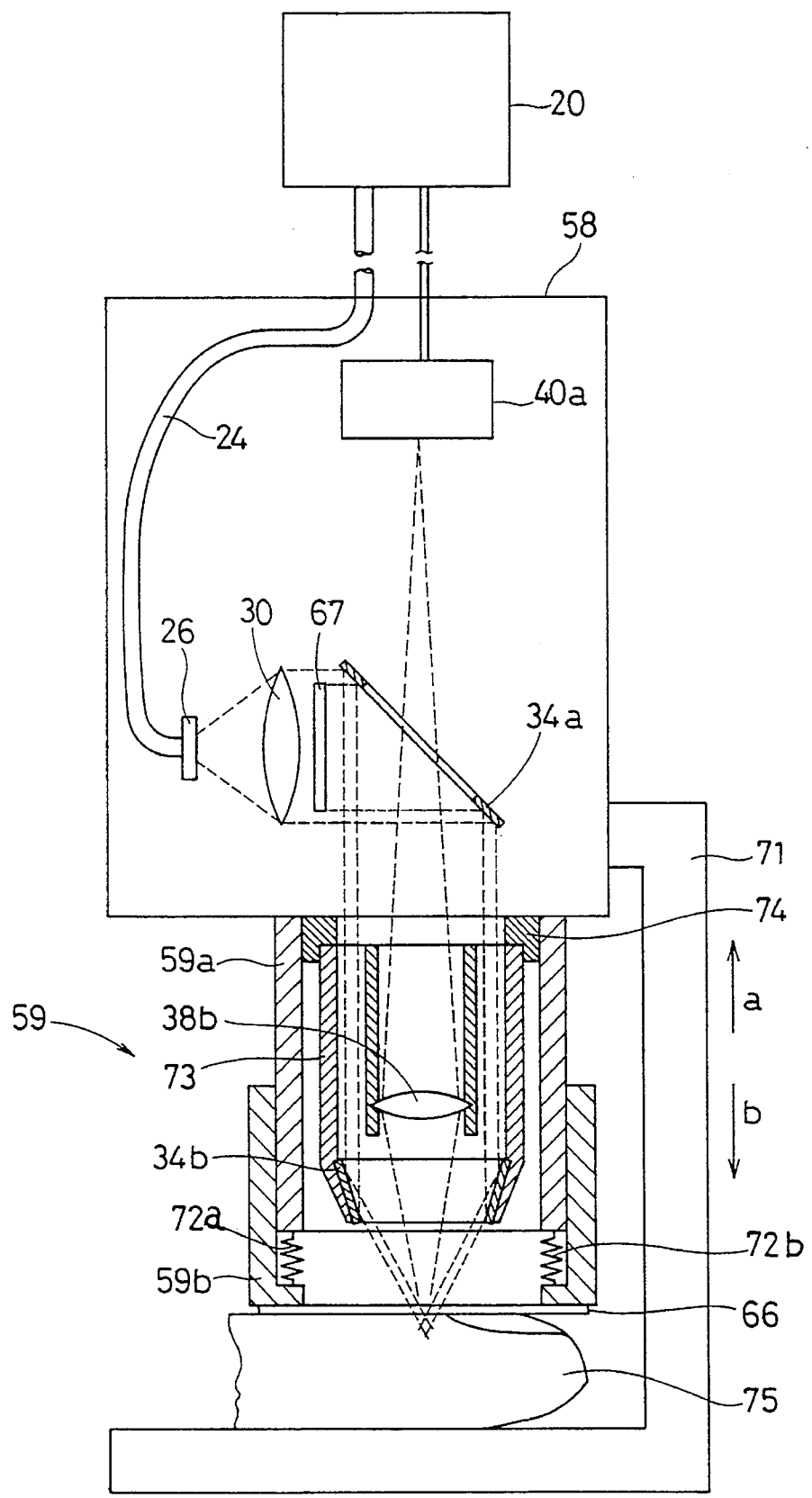
FIG. 21 is a view showing a modification of embodiment 4 shown in FIG. 20.

Desirably, the non-invasive blood analyzer provides fixing means for relatively fixing at least part of the living body and the imaging means and stabilizing means for stabilizing the focus of the imaging means with respect to the detection region in order to exactly apply the light from the light application means to the detection region in the vessel and clearly photograph the detection region. For this purpose, more preferably, the blood analyzer of the present invention provides integrally or separately the fixing means and the stabilizing means. The structure of such means can be appropriately designed in consideration of the analyzer and the part containing the detection region. The structure thereof can also be determined in consideration of the configuration and size of the living body portion where the detection region exists. For example, when the detection region is contained in a capillary vessel in a lip, means as shown in FIG. 17 can be used. In addition, when the detection region is contained in a capillary blood vessel in a finger, means as shown in FIG. 21 can be used.

The present invention will be detailed in conjunction with the preferred embodiments, which are not intended to limit the scope of the present invention.

Embodiment 1

FIG. 1 is a view illustrating a structure of embodiment 1 of the present invention. As shown in FIG. 1, light application means for applying light to a detection region V in a blood vessel 12 that exists inside of a skin surface 16 of a living body comprises a laser light source 22, an optical fiber 24, and a slit 60. Additionally, an imaging means comprises a CCD 40 provided with a one hundred thousandth ($10^{-5}$) of a second electronic shutter, a lens 38, a polarizing filter 61 and a video system 44.

Then, analysis means which processes images captured with the CCD 40 provided on the imaging means, analyzes the morphology of blood cells contained in the detection region V and counts the number thereof comprises an image processing circuit 46, means 48 for counting the number of red blood cells, means 50 for calculating MCV, means 52 for calculating HGB, means 54A for calculating HCT, means 54B for calculating MCH, means 54C for calculating MCHC, means 56A for calculating the number of white blood cells, means 56B for classifying white blood cells and means 57 for calculating the blood flow rate.

Figure 2:
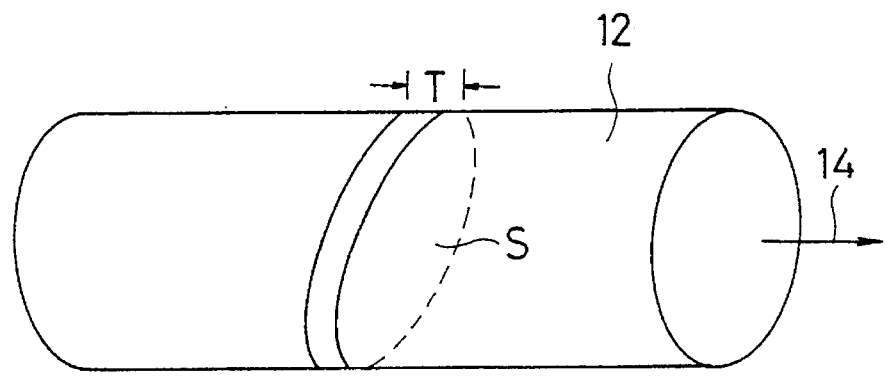
FIG. 2 is a view showing an example of a detection region.

Then, the CCD 40 forms one image frame each time the CCD captures the detection region V irradiated with a laser at a shutter speed (capturing time) of one hundred thousandth of a second ($10^{-5}$ sec). In this embodiment, as shown in FIG. 2, the light application means forms the thin disk-like detection region V having a cross section S and a thickness T with a slit shaped beam of light applied to the blood vessel 12 in a direction diagonal with respect to the direction of the blood stream of the blood vessel 12 so as to image blood cells that exist in the detection region V. Incidentally, in FIG. 1, a subcutaneous portion (below the skin 16) of the living body is magnified for convenience.

The light source 22 is accommodated in an analyzer 20. The tip of the optical fiber 24, the slit 60, the CCD 40, the lens 38, the polarizing filter 61 are all accommodated in a probe 58. Laser light fired from the light source 22 is regulated with the slit 60 after coming out of the tip of the optical fiber 24 and is translated into a thin belt-like (slit-shaped) optical beam having a thickness T to irradiate the living body. A transparent plate 66 made of plastic or glass is provided to give a stable image by allowing a tip 59 of the probe 58 to closely contact the skin surface 16.

When the belt-like optical beam traverses the blood vessel 12, a specific region of the blood vessel is irradiated to form a detection region V. The reflected light coming from the detection region V is received at a light receiving surface of the CCD 40 via the polarizing filter 61 and the lens 38. The resulting captured image is recorded in the video system 44 via a transmission cable 42. Here the "swing and tilt" photography technique is used to capture a reflection of light coming from a cross section 62 having a thin disk-like configuration. Since the cross section 62, the lens 38 and the CCD 40 are disposed at positions that enable the swing and tilt photography technique, a clear image in focus is provided.

The area S of the cross section 62 is determined by dividing the square of the capturing magnification into the image area on the captured cross section. Since the thickness T which represents the thickness of the belt-like optical beam is already known from the slit width of the slit 60, the volume of the region V can be calculated.

Furthermore, the volume of the region V may be determined by cutting the captured image of the imaged cross section with a window having a predetermined area, dividing the square of the imaging magnification into the window area and multiplying the value thus given by the thickness T.

Since the thickness T of the region V is set to a small value, for example, on the order of 10 microns, a probability is not so high that blood cells overlap a flat image captured with the CCD. Even if the blood cells overlap the flat image, it is still easy to differentiate each of the blood cells on the image with the image processing technique.

Incidentally, it is possible to calculate the number of blood cells from one frame of the image as described above. In this embodiment, tens of frames of images to hundreds of frames of images are continuously captured to enhance the accuracy in the analysis. In other words, although a distribution of blood cells should be essentially determined from a wide scope of blood vessels to calculate each of the above indices based on the determined distribution, it is found that the distribution of blood cells can be determined from a large number of images obtained by the continuous capturing of the same detection region to statistically calculate each reliable index based on the distribution thus determined.

When an image intensifier provided with a high speed gate is adopted into the imaging means, a clear image can be obtained even when the amount of light application to the blood vessel is small. Thus the light source may have such a low power that the light application to the living body might not cause a burn thereon.

As shown in FIG. 1, the handling of the optical system can be facilitated by integrally accommodating all the equipment of the optical system in the single probe 58. Thus images of blood cells can be captured and measured only by placing the tip of the probe 58 on the surface of the skin 16 via the transparent plate 66.

FIG. 17 is a view illustrating a state of measuring a blood vessel in a lip by attaching the probe 58 to an attaching device to fix the probe 58 to a subject. A forehead fixing part 100*a* fixes a probe attaching device 100 to the forehead of the subject, and a jaw fixing part 100*b* fixes the probe attaching device to the jaw of the subject. When the probe 58 is allowed to closely contact the lip as a detection region via stabilizing means, for example, a transparent plate 66 by using the probe attaching device as shown in FIG. 17, the friction of the transparent plate 66 causes the tip of the probe 58 to be fixed on the skin surface of the subject to suppress the relatively fine vibration between the tip of the probe 58 and the lip portion thereby stabilizing the focus of the imaging system and preventing the detection region from mechanically shifting with respect to the imaging system.

Furthermore, providing the polarizing filter 61 on the light receiving system enables the removal of unnecessary components of scattered light to give a good image having a good contrast. Even if no polarizing filter is mounted on the light application system at this time, the filter on the light receiving system can improve the contrast of the image to a considerable degree. Preferably, the light application system includes a polarizing filter. A method may be used which involves introducing a polarized laser beam through a polarized wavefront protection fiber.

Figure 3:
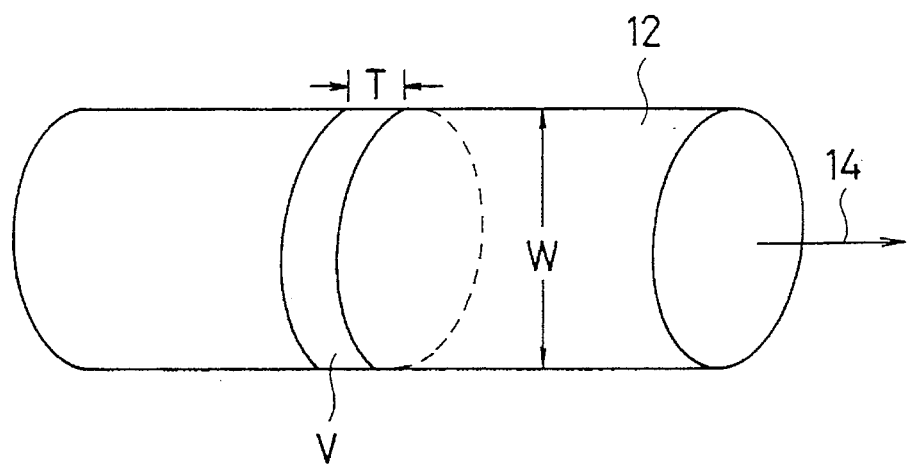
FIG. 3 is a view showing an example of a detection region.

In FIGS. 1 and 2, the volume region V for detection is formed in a disk-like configuration diagonally with respect to the direction of the blood stream through the blood vessel 12. However, as shown in FIG. 3, the region V may be formed in a disk-like configuration having a diameter W and a thickness T disposed orthogonally with respect to the direction of the blood flow. In this case, like FIG. 1, an image of the vessel vertically sectioned in the direction of the blood stream will be captured in the swing and tilt photography. The diameter W is determined by the diameter of the blood vessel. The thickness T is determined by the beam width of the light application system. When the disk-like cross section of the blood vessel is similar to a complete circle, the area of the cross section can be simply determined from the diameter W. When the cross section is deviated from a complete circle, the area of the cross section may be determined in the same manner as shown in FIG. 2.

Figure 4:
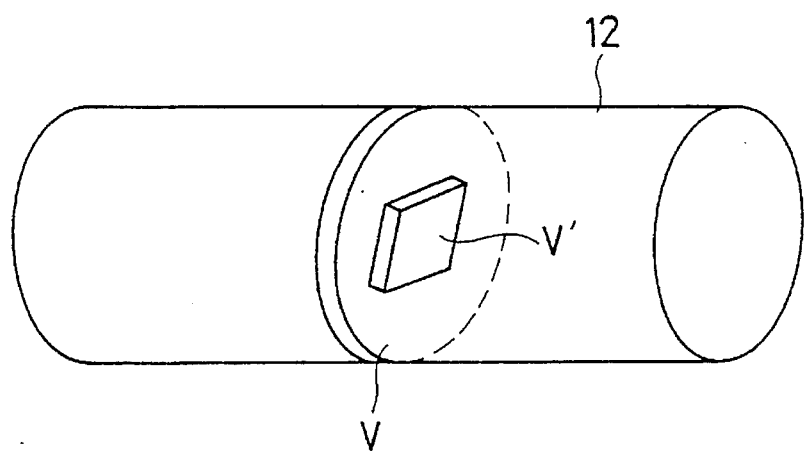
FIG. 4 is a view showing an example of the detection region.

In FIGS. 2 and 3, the entire region V cannot be accommodated in the capturing screen. In other words, as shown in FIG. 4, only a region V' which constitutes part of the region V is displayed on the entire surface of the screen. In such case, the entire portion displayed on the screen can be regarded as a magnified image of the detection region V (V' is regarded as V).

In this manner, the dynamic state of the blood cells flowing through the blood vessels can be captured from the direction of the blood stream.

Referring to FIG. 1, the video system 44 provides a video recorder (VTR) for recording an image captured with the CCD 40. The recorded image is processed at the image processing circuit 46 and is sent to means 48 for calculating the number of red blood cells, means 50 for calculating MCV, means 52 for calculating HGB, means 54A for calculating HCT, means 54B for calculating MCH, means 54C for calculating MCHC, means 56A for calculating the number of white blood cells, means 56B for classifying white blood cells, and means 57 for calculating the flow rate of blood thereby analyzing the morphology (including the tone) and/or number of the blood cells to calculate each of the items of the blood test. In addition, the image processing circuit 46 selectively provides the functions of each kind of filter, color tone correction, interpolation, jitter correction, tone conversion, color balance correction, white balance, and shading correction to perform pretreatment of images. Subsequently, the means 48 for calculating the number of red blood cells will be detailed hereinafter.

Figure 8:
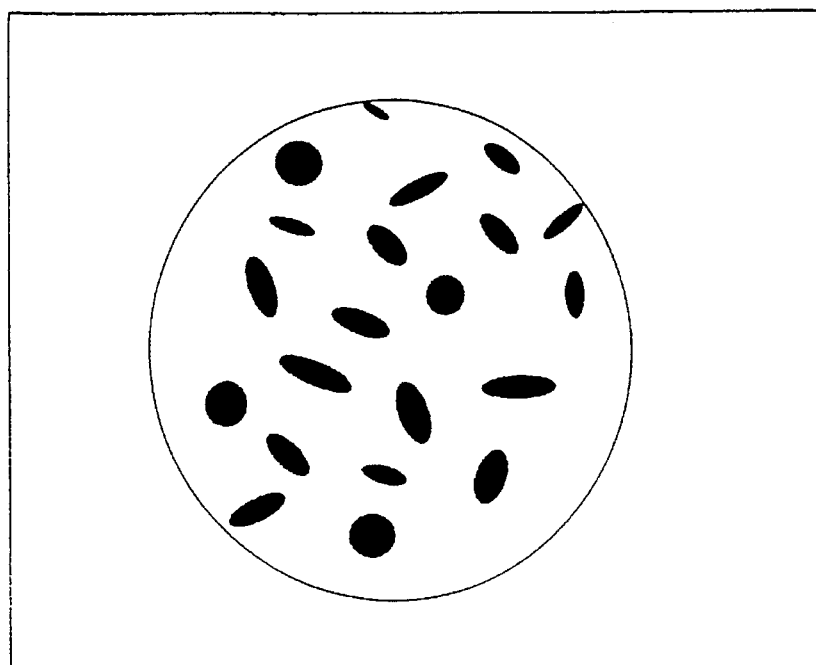
FIG. 8 is a view illustrating a captured image.
Figure 9:
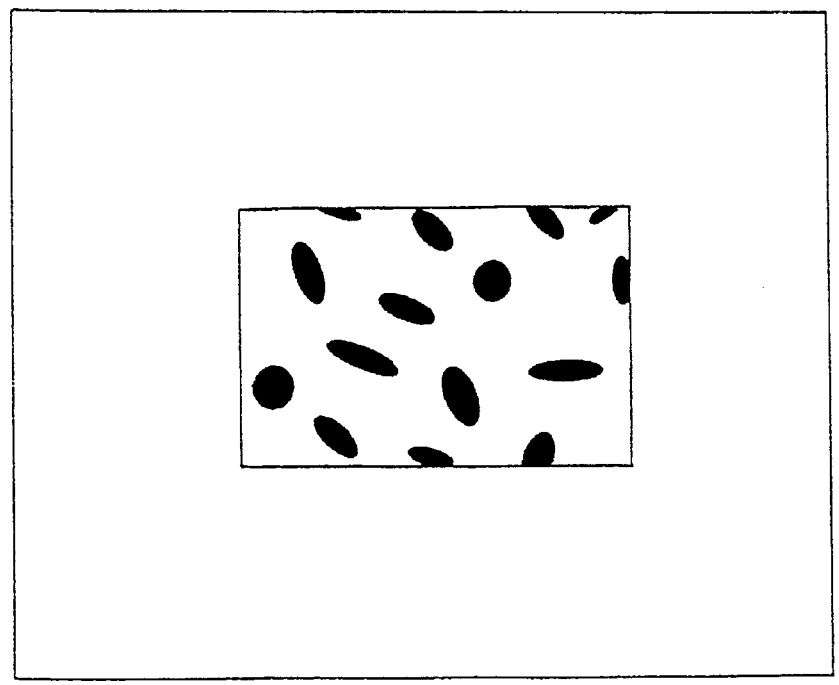
FIG. 9 is a view showing a state in which an image is cut with a window.
Figure 10:
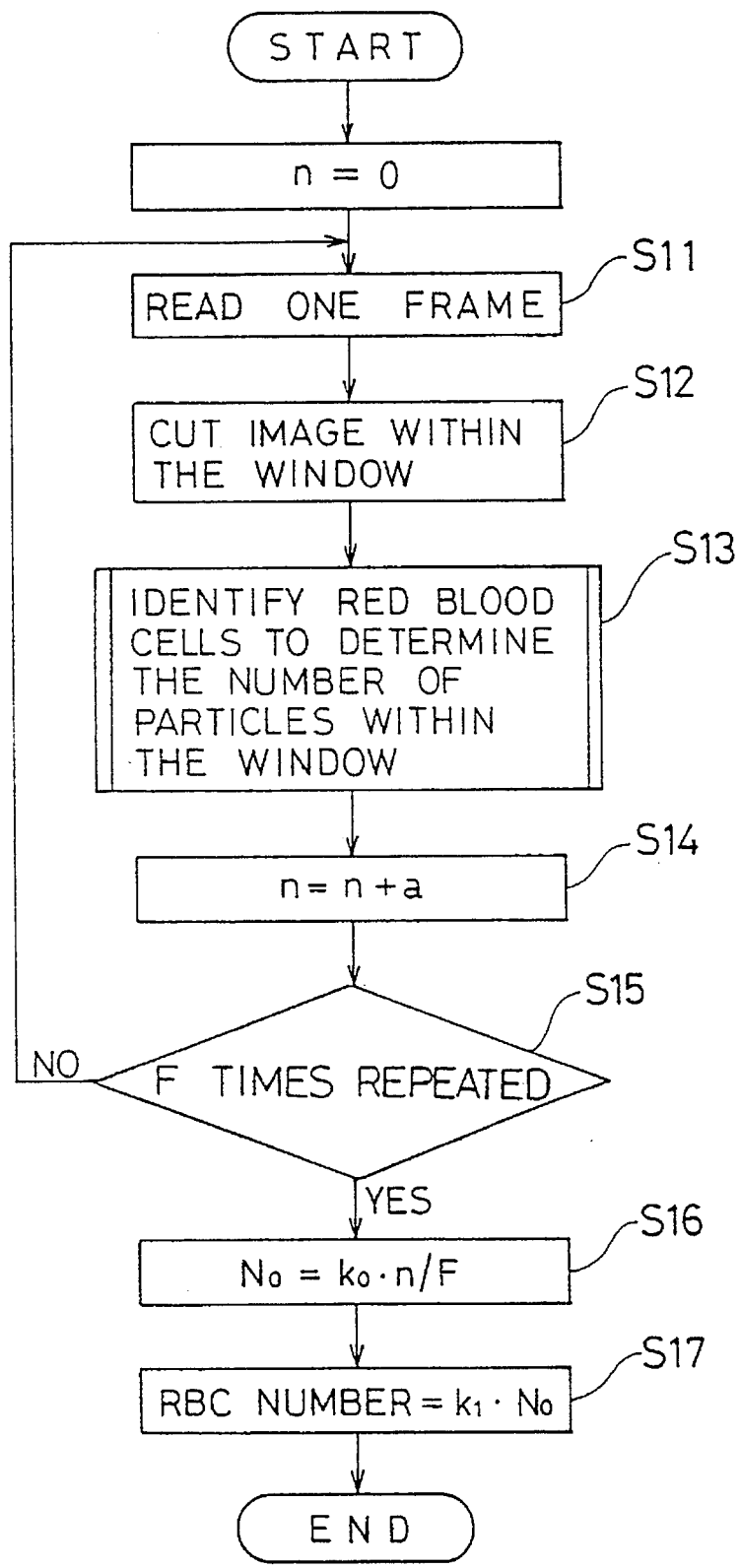
FIG. 10 is a flowchart showing a procedure for calculating the number of red blood cells.

The means 48 for calculating the number of red blood cells calculates the number of red blood cells (RBC) per unit volume by counting the number of red blood cells in images of the region V. The procedure of the calculation is shown in the flowchart in FIG. 10. In FIG. 10 a frame of an image in which the region V is captured is read one by one from the video system 44 as shown in FIG. 8 (step 11), followed by cutting the read image with a window having a predetermined size as shown in FIG. 9 (step S12), and identifying red blood cells in the window to determine the number a of red blood cells in the window (step S13). This operation is repeated by a predetermined number F of frames to determine the sum n of the number a of red blood cells obtained in each operation (steps S14 and S15) thereby calculating the mean red blood cell per unit volume represented by $N_0 = K_0 \cdot n/F$ (step S16). In the formula, symbol $K_0$ is a conversion constant determined from the window size, the capturing magnification and the thickness T of the region V. When necessary, No is multiplied by a correction constant $K_1$ to translate data on arterioles and veinlets (capillary vessels) into the number of red blood cells (RBC) corresponding to the medium-size and large blood vessels (step S17). When necessary, with respect to the image processing of red blood cells at step S13, a known method can be used (for example, see "An Algorithm of Automated RBC Classification and Its Evaluation" Akihide Hashizume et al, Medical Electronics and Bio-Engineering Vol. 28, No. 1, March, 1990). Two continuous captured images in which red blood cells moved by approximately 0.1 micron (showing a time lag of one hundred thousandth of a second at the blood stream of 10 mm per second) is subjected to subtraction processing so that red blood cells can be identified at a higher speed from a two dimensional differentiated image in which only edges of moving red blood cells are emphasized.

Figure 11:
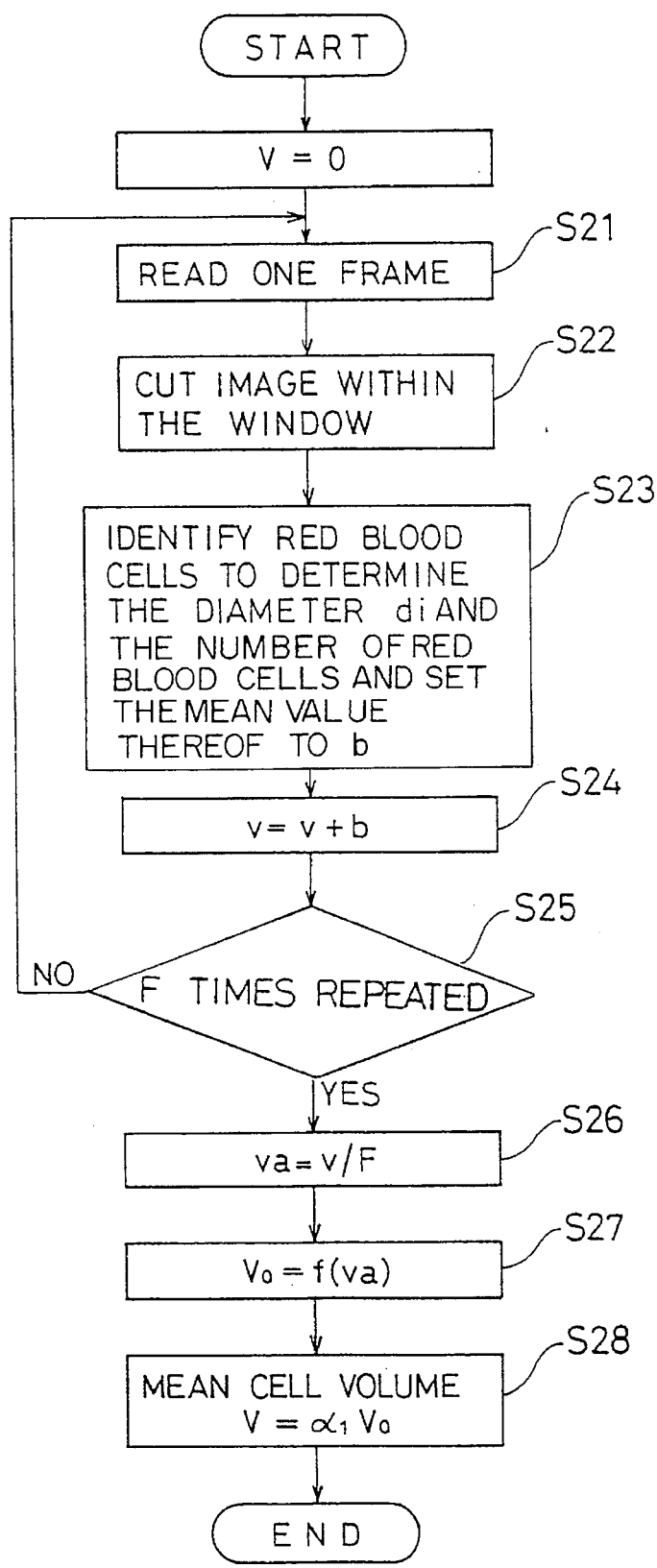
FIG. 11 is a flowchart showing the procedure for calculating MCV.

Subsequently, the means 50 for calculating MCV will be explained hereinafter. The means 50 determines the mean corpuscular volume (MCV) by determining an area of each red blood cell from the image and multiplying the mean value of the area of each red blood cell by a predetermined constant to calculate the volume value; The procedure is shown in the flowchart in FIG. 11. In FIG. 11, a frame of an image is read by one by one from the video system 44 (step 21) followed by cutting the image thus read with a window having a predetermined size (step 22) and identifying red blood cells in the window to determine the diameter di thereby calculating the mean value b thereof (step S23). The same operation is repeated by the predetermined number of frames F to determine the sum V of the mean values b obtained in each operation (steps S24 and S25). The sum V is divided by the number F of frames to calculate the mean diameter Va (step S26) to determine the volume $V_0$ by using a function f (experimentally determined function) for translating the diameter into the volume (step S27). Then the volume $V_0$ thus given is multiplied by a correction constant a1 to determine the mean corpuscular volume (MCV) corresponding to the medium-size and large arteries and veins from data on the arterioles and veinlets as well as capillary vessels (step S28). Here the reason why the mean diameter Va is calculated by the V/F in step S26 is that the number of erythrocytes identified in step S23 is assumed to be approximately the same in each frame.

Then, means 52 for calculating the amount of hemoglobin will be explained hereinbelow. The means 52 calculates the total amount of hemoglobin (HGB) per unit area from the intensity of light incident to the region V and the intensity of light reflected at the region V in accordance with the following principle.

When the intensity of incident light is represented by $I_0(\lambda)$ and the intensity of the reflection light by $I(\lambda)$, the following formula is established:

$$I(\lambda) = I_0(\lambda)^o \alpha(\lambda) \times \exp((\epsilon_1(\lambda) HgbO_2 + \epsilon_2(\lambda) Hgb)) \quad (1)$$

where $\alpha(\lambda)$ represents a scattering term (which depends on the wavelength), $\epsilon_1(\lambda)$ an absorption constant of oxyhemoglobin (which depends on the wavelength), $\epsilon_2(\lambda)$ an absorption of deoxyhemoglobin (which depends on the wavelength), $HgbO_2$ a concentration of oxyhemoglobin, Hgb a concentration of deoxyhemoglobin and $\lambda$ a wavelength.

The total amount of hemoglobin HGB per unit volume is determined by the formula:

$$HGB = HgbO_2 + Hgb. \quad (a)$$

The scattering term of formula (1) can be regarded approximately as a constant by appropriately selecting a predetermined wavelength $\lambda$. When the scattering term is represented by $\alpha_0$, the formula (1) can be represented as $$\log(I(\lambda)/I_0(\lambda)) = (\epsilon_1(\lambda) HbO_2 + \epsilon_2(\lambda) Hg) + \log \alpha_0 \quad (b)$$

By the way, $I(\lambda)/I_0(\lambda)$ is a value obtained in the measurement. Then $\epsilon_1(\lambda)$ and $\epsilon_2(\lambda)$ become a constant with respect to the selected wavelength, and three values such as $HgbO_2$, Hb, and $\alpha_0$ are given as unknown values.

Therefore, the following results are produced.

(a) Two values $HgbO_2$ and Hgb are determined by measuring $I(\lambda)/I_0(\lambda)$ with respect to appropriate three wavelengths.

(b) When $\alpha_0$ does not depend on living bodies and is assumed to be definite, two values $HgbO_2$ and Hgb can be determined by measuring the two values on condition that $\alpha_0$ is preliminarily determined in tests (there is no problem for practical purposes when $\alpha_0$ is assumed to be definite).

(c) Furthermore, selecting a wavelength (for example, 525 nm) at which the oxygen type and the deoxygen type Hgb have the same light absorbance produces a result of $\epsilon_1(\lambda) = \epsilon_2(\lambda)$. The total amount of hemoglobin per unit volume can be determined by the wavelength.

Incidentally, in the field of blood analysis, the total amount of hemoglobin is simply referred to as hemoglobin. Thus the amount will be described as such hereinbelow. In accordance with the above principle, the means 52 for calculating hemoglobin calculates HGB. The calculation follows any of the three procedures shown in the flowchart in FIGS. 12 to 14.

Figure 12:
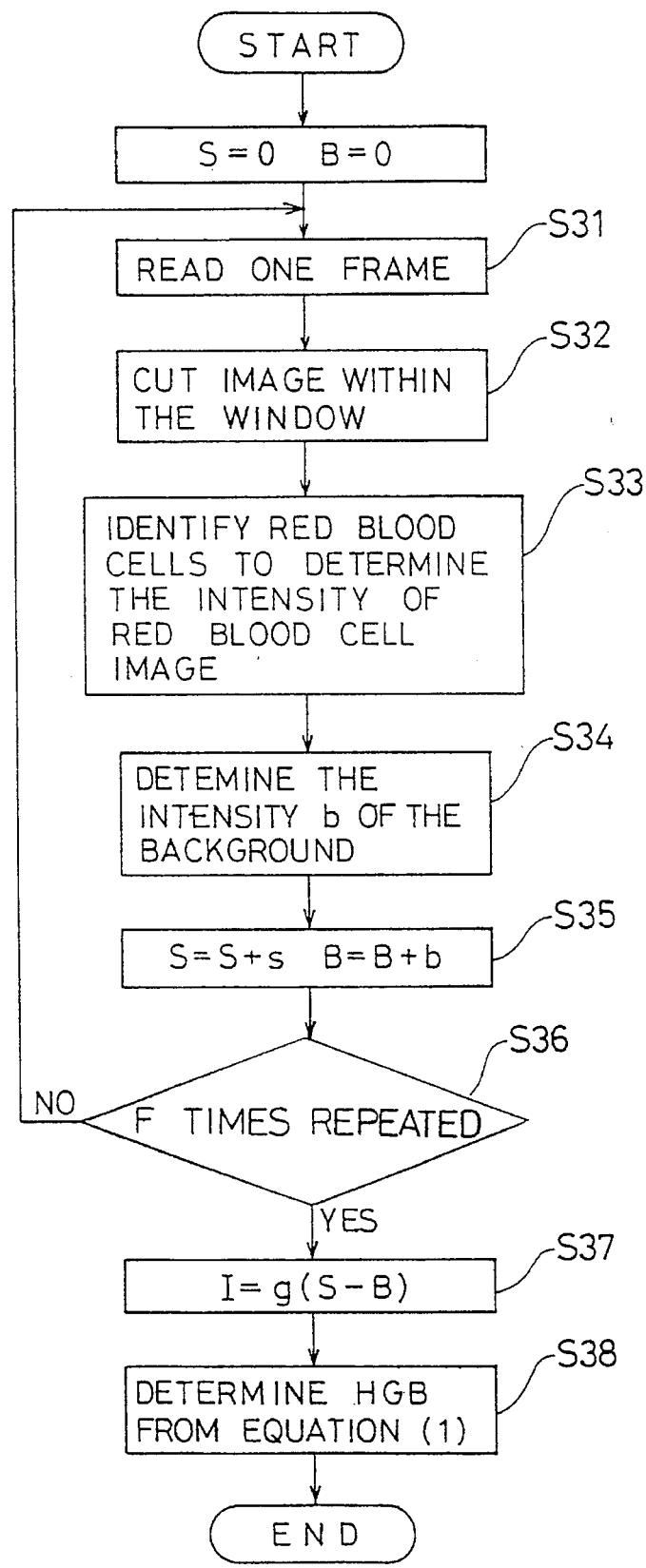
FIG. 12 is a flowchart showing a procedure for calculating hemoglobin.

At the outset, the procedure shown in FIG. 12 is characterized by determining the intensity $I(\lambda)$ of reflection light from the sum of the intensity of images. In other words, each image frame is read from the video system 44 (step S31), cutting the read image with a window having a predetermined size and recognizing red blood cells within the window to determine the intensity s of the red blood cell image. Then, the intensity b at the background of the image is determined (step S34).

Each of the sums S and B of the intensity s and b is determined which is thus obtained by repeating the above operation by the predetermined number F of frames (steps S35 and S36). Then the intensity $I(\lambda)$ is calculated by the function g with which the intensity $I(\lambda)$ is determined from a difference between S and B (step S37). Incidentally, function g was experimentally determined. Then the hemoglobin and HGB are determined by the formula (1) on condition that $I_0(\lambda)$ is already known (step S38).

Figure 13:
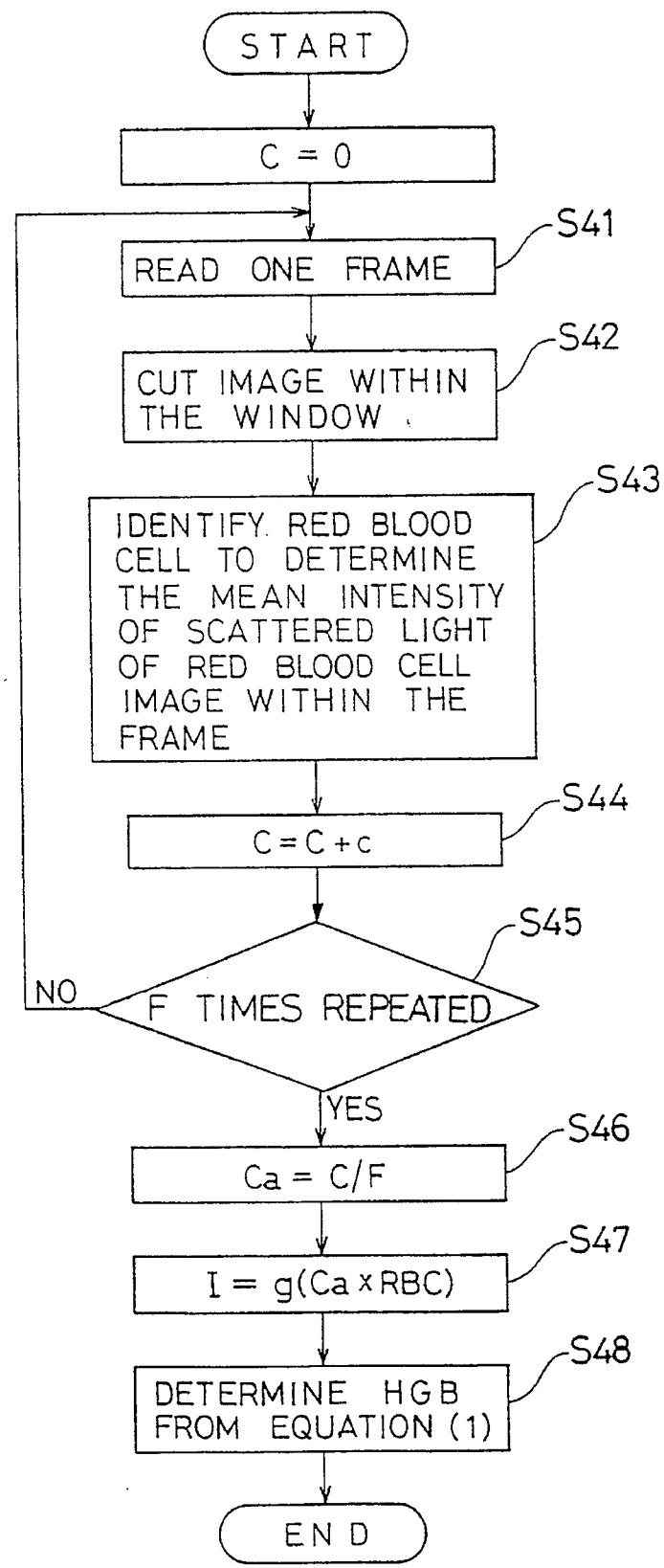
FIG. 13 is a flowchart showing the procedure for calculating hemoglobin.

Then, the procedure shown in FIG. 13 is characterized by determining the intensity $I(\lambda)$ of the reflected light from the mean concentration of red blood cells. In FIG. 13, each image frame is read from the video system 44 (step S41) followed by cutting the read image with a window having a predetermined dimension (step S42), identifying red blood cells within the window, and determining the mean scattered light intensity (step S43). The sum C of the intensity c is determined which is obtained in each operation by repeating the above operation by the predetermined number F of frames (step S44 and S45) followed by calculating the mean scattered light intensity Ca with respect to one red blood cell (step S46). Then $I(\lambda)$ is determined by using a function (experimentally determined) in which $I(\lambda)$ is determined from the mean intensity Ca and the red blood cell number (RBC) (step S47). Given that $I_0(\lambda)$ is already known, hemoglobin (HGB) is determined from the formula (1) (step S48).

Incidentally, one of the above procedures (shown in FIG. 12 and FIG. 13) which has a smaller difference between frames can be adopted by executing either the procedure shown in FIG. 12 or the procedure shown in FIG. 13. When the light source 22 applies light having two wavelengths, either the procedure shown in FIG. 12 or the procedure shown in FIG. 13 is executed with respect to each wavelength to determine the hemoglobin based on formula (1). In such case, oxygen hemoglobin and the deoxygen hemoglobin can be respectively determined.

Figure 14:
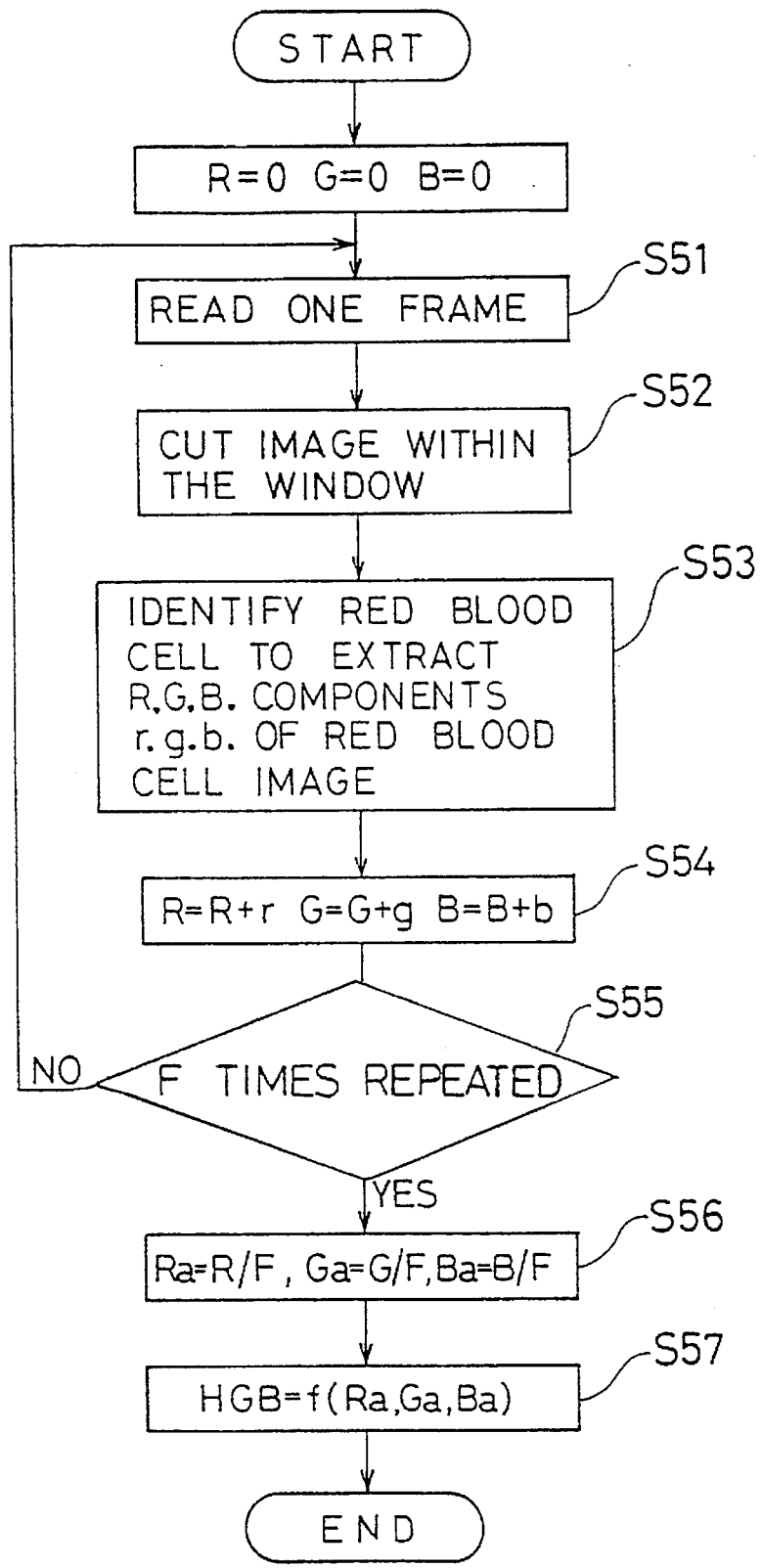
FIG. 14 is a flowchart showing the procedure for calculating hemoglobin.

Subsequently, the procedure shown in FIG. 14 is characterized by determining the hemoglobin from the tone of the image when light is applied which has three wavelengths, a white color or a wide band spectrum. In FIG. 14 each image frame is read from the video system 44, the read image is cut with a window having a predetermined size, and red blood cells in the window are identified while each component r, g and b of R (red), G (green) and B (blue) colors in the red blood cell image is extracted (steps S51, S52 and S53). The above operation is repeated by a predetermined number F of frames to calculate the respective sum R, G, and B of component r, g and b obtained in each operation (steps S54 and S55). Then the mean original color components Ra, Ga and Ba are determined (step S56) to calculate hemoglobin HGB by using a function of experimentally determined in advance (step S57).

Subsequently, the means 54A for calculating a hematocrit value will be detailed herein after. The means 54A calculates the following equation to determine the hematocrit value HCT.

$$HCT = \alpha_2 \times (MCV) \times (RBC) \quad (c)$$

Here, MCV is a value determined at the means 50 for calculating MCV whereas RBC is a value determined at the means 48 for calculating the number of red blood cells. Then $\alpha_2$ is a correction constant for translating a value corresponding to veinlets into a value corresponding to medium-size to large arteries and veins.

Then, the means 54B for calculating the mean corpuscular hemoglobin (MCH) calculates the following equation to determine the mean corpuscular hemoglobin (MCH).

$$MCH = (HGB)/(RBC) \quad (d)$$

where HGB is a value determined by the means 52 for calculating the hemoglobin, and RBC is a value determined by the means 48 for calculating the number of red blood cells.

The means 56A for calculating the number of white blood cells will now be explained. The means 56A calculates the number of white blood cells per unit volume by recognizing white blood cells in images of the region V and counting the number thereof. Since the procedure for calculating the number thereof is the same as the counterpart for calculating the number of red blood cells (RBC) as shown in FIG. 10, detailed description thereof is omitted here. The number F of frames has to be increased in the case of counting the white blood cells because the number of white blood cells is smaller than that of red blood cells (about one thousandth).

Figure 15:
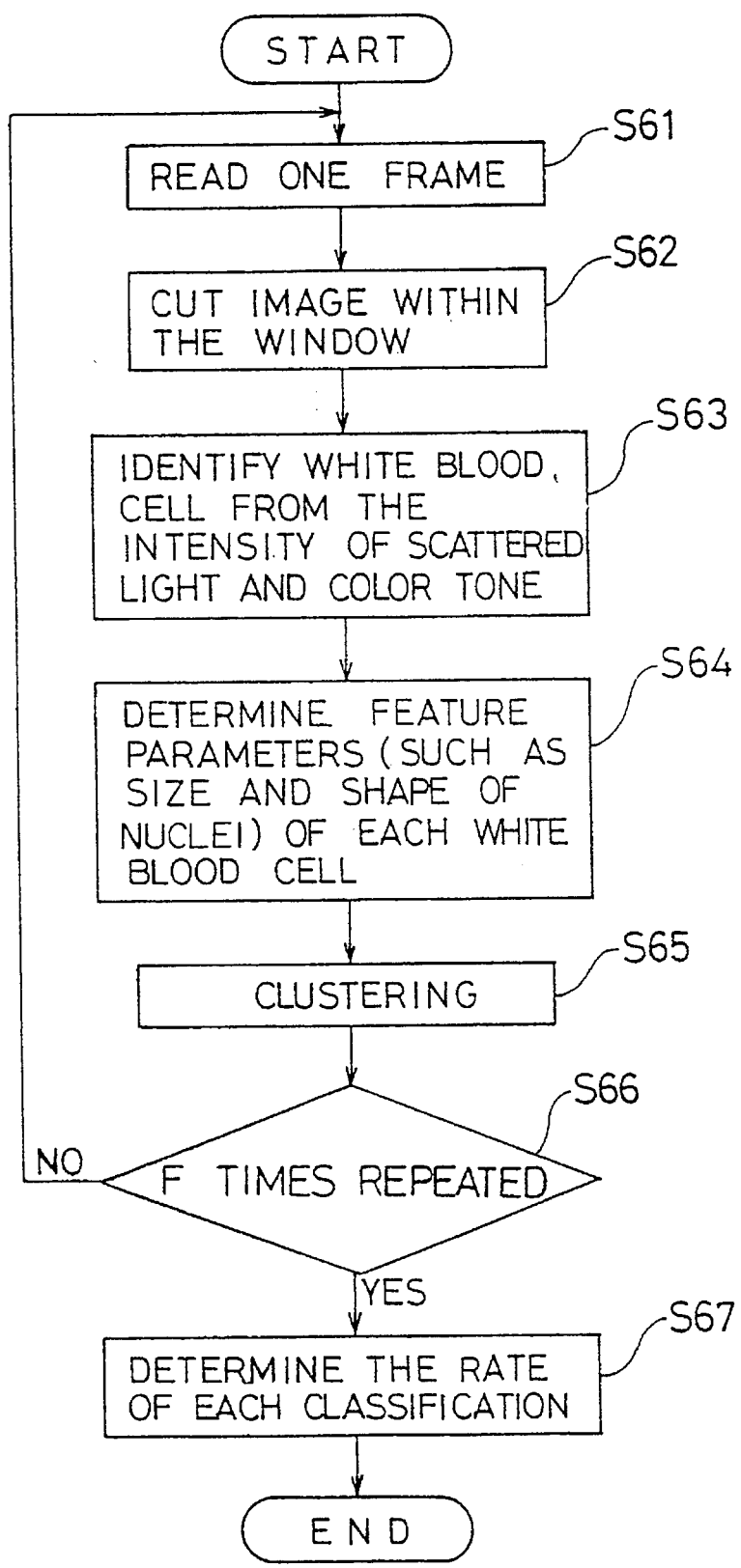
FIG. 15 is a flowchart showing a procedure for classifying white blood cells (leukocytes).

The means 56B for classifying white blood cells will now be described. The means 56B classifies white blood cells into lymphocytes, monocytes, neutrophil, eosinophil and basophil from morphological features. The procedure thereof is shown in the flowchart of FIG. 15. In FIG. 15 an image frame is read from the video system 44 (step S61), the read image is cut with a window having a predetermined size (step S62), and white blood cells in the window are recognized from the strength of scattered light and color tone (step S63). Then the feature parameters (such as size, shape, size of nuclei, shape of nuclei) of individual white blood cells are determined (step S64), and the classification is made in accordance with the determined feature parameters (step S65). The above operation is repeated by the predetermined number F of frames to calculate each classification ratio (step S67).

Figure 16A:
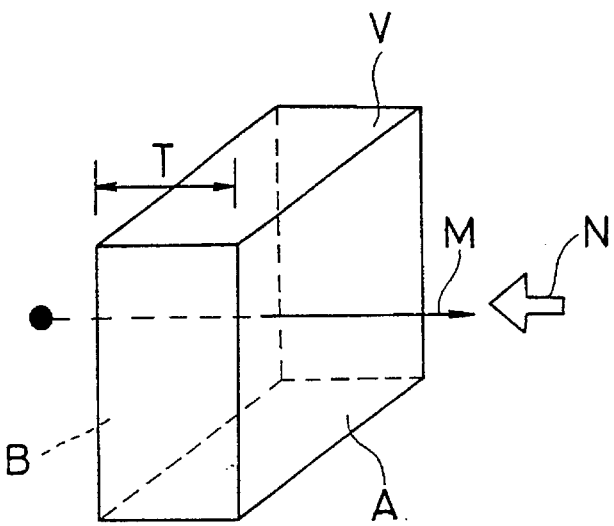
FIGS. 16(a) through 16(d) are views illustrating the principle of calculating the flow rate of blood.
Figure 16B:
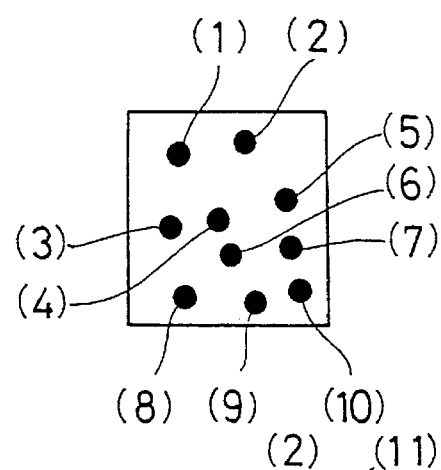
Figure 16C:
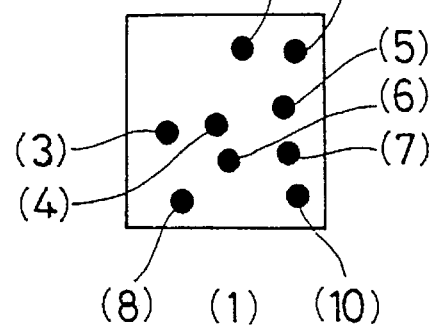
Figure 16D:
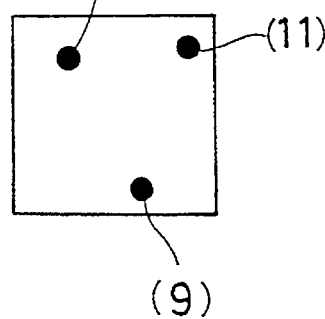

Then means 57 for calculating the rate of blood stream will be detailed hereinbelow. The means 57 can, as shown in FIGS. 2 and 3, provide a cross-section image of blood vessels thereby enabling the calculation of the rate of blood stream with the principle (zero-cross method expanded in space). In other words, when the particles pass through the detection region partitioned with parallel planar surfaces A and B spaced by T in the direction M as shown in FIG. 16(a), the traveling particles are observed from the direction N. Referring to FIG. 16(b), ten particles are observed at time t. After time $\Delta t$, particles (1) and (9) located near the surface A get out of the region V. When a particles (11) located in the neighborhood of the surface B enter the region V, particles that appear and disappear in time $\Delta t$ with respect to the region V becomes apparent as shown in FIG. 16(d) based on a difference between FIGS. 16(b) and 16(c). Then, assuming that the distribution density of the particles is definite, the frequency of appearance is proportional to the speed of the particles. In other words, when the speed is high, the frequency is high. When the speed is low, the frequency is low.

Suppose that the mean observed particle number is designated by Na, and the mean number of the particles that appear at time t and t+$\Delta t$ by Aa, particles go out of the region by Aa/2 during time $\Delta t$. Time required for all the number Na of particles to move by distance T is represented by a formula:

$$2\Delta t \cdot Na/Aa. \text{ The average speed Xa of the particles is given by}$$
$$Xa = T \cdot Aa \, (2\Delta t \cdot Na)j \quad (2)$$

where $\Delta t$ is a preset value, and T is a known value.

The means 57 uses this principle to allow the determination of Na and Aa with respect to captured red blood cells by reading an image from the video system 44, and the calculation of the rate of blood stream from equation (2).

Any information on each kind of blood cell (calculated value) can be translated into blood information that has been clinically used for the medium and large arteries and veins by multiplying the results with an experimentally determined correction constant.

Embodiment 2

Figure 5:
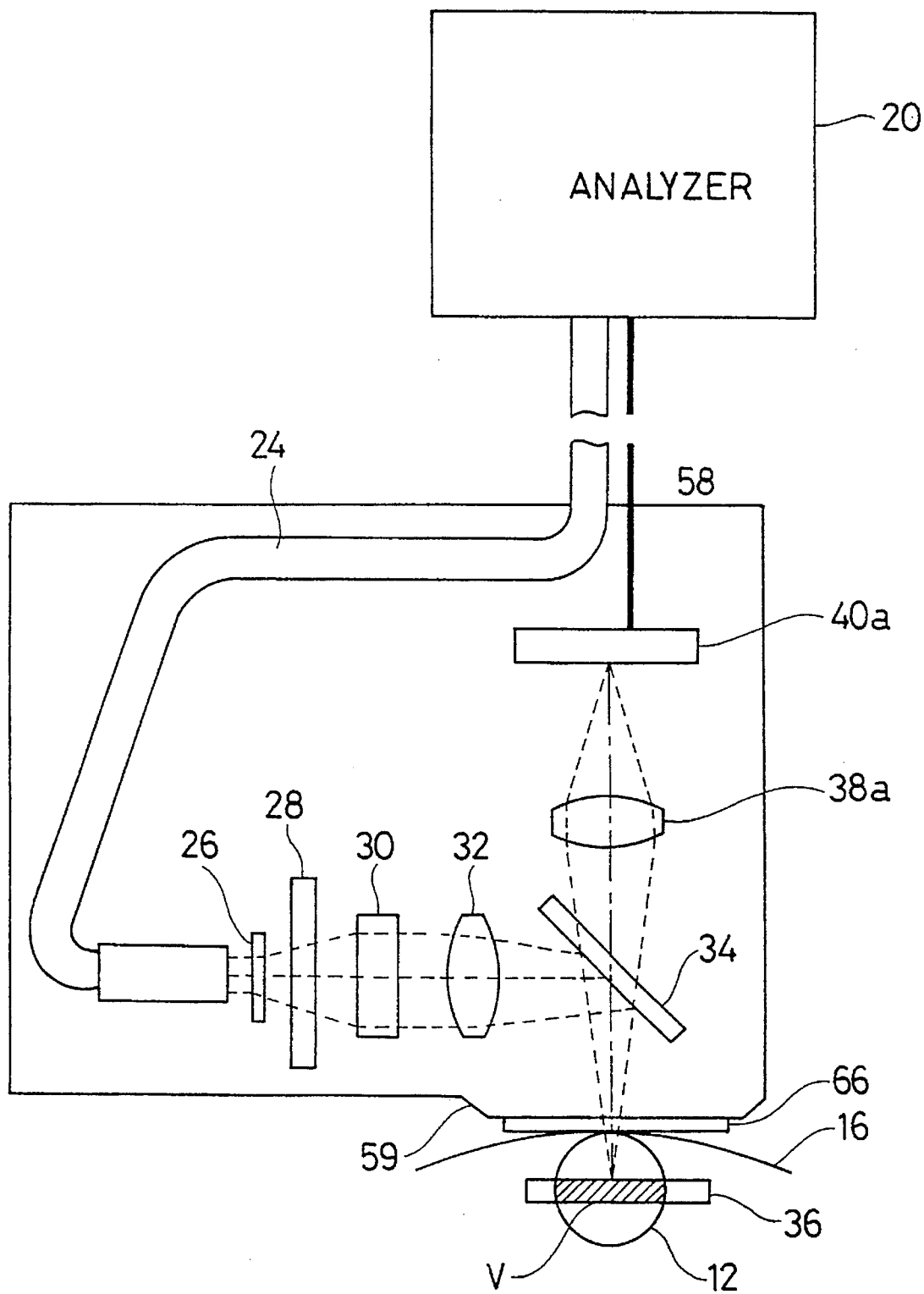
FIG. 5 is a view illustrating the structure of embodiment 2 of the present invention, the view showing an essential portion thereof.
Figure 6:
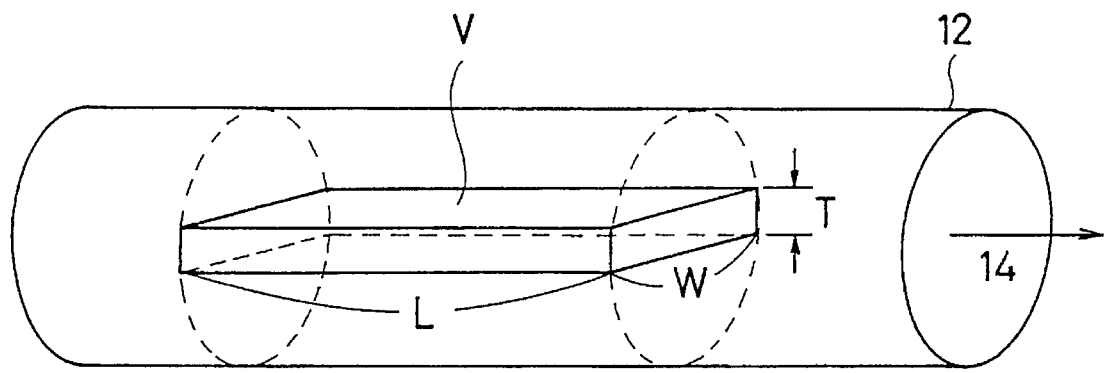
FIG. 6 is a view showing an example of a detection region.

FIG. 5 is a view showing a structure of embodiment 2 of the invention, the view showing an essential portion of the embodiment 2. FIG. 6 shows a case in which the light application means forms a thin belt-like detection region V having a width of W, a length of L and a thickness of T in parallel to the direction 14 of the blood stream through the vessel 12 thereby counting the number of blood cells that are present in the region V. Also in FIG. 5, a portion below the skin surface 16 is magnified for simplicity. Referring to FIG. 5, the direction of the blood stream is perpendicular to the paper surface. The main body of the analyzer 20 is the same as FIG. 1, so the drawings thereof is omitted here.

The light generated from the light source 22 in the main body of the analyzer 20 irradiates the diffuser 26 via an optical fiber 24. Light is diffused with the diffuser 26 to uniformly irradiate a plate 28. The plate 28 substantially forms a surface light generator so that an real image of the plate 28 is formed across the blood vessel 12. Incidentally, as the plate 28, an optical diffusion plate, for example, a frost type diffusion plate manufactured by Sigma Optical Materials Co., Ltd. is used.

The real image 36 of the plate 28 has a thickness of T. A region where the real image 36 of the plate 28 intersects the blood vessel 12 forms the detection region V.

Preferably, the real image 36 is compressed so that the width of the real image 36 is identical to the diameter of the blood vessel and thereby blood cells in the blood vessel can be clearly imaged by the CCD 40a, since the irradiation is highly concentrated on the real image 36, and moreover, the blood cells do not overlap each other in the real image 36.

The width W of the region V is identical to the diameter of the blood vessel in FIGS. 5 and 6. The region V shown in FIG. 5 has a length of L in the direction of the paper surface (see FIG. 6). The length L is determined by the degree of aperture of the light application system.

The CCD 40 a receives the light reflected at the region V via a dichroic mirror 34 and a lens 38a. Analyzing an image captured with the CCD 40a enables the determination of values in each item of hematology test from the morphological analysis and the number of blood cells in images in the region in the same manner as FIGS. 1 and 2.

Incidentally, FIGS. 5 and 6 show a case in which the real image 36 of the plate and the blood vessel 12 intersect each other. When the diameter of the blood vessel is thick, the real image 36 of the plate 28 may be formed completely inside of the blood vessel 12. In such case, the real image 36 of the plate itself constitutes the detection region V.

Figure 7:
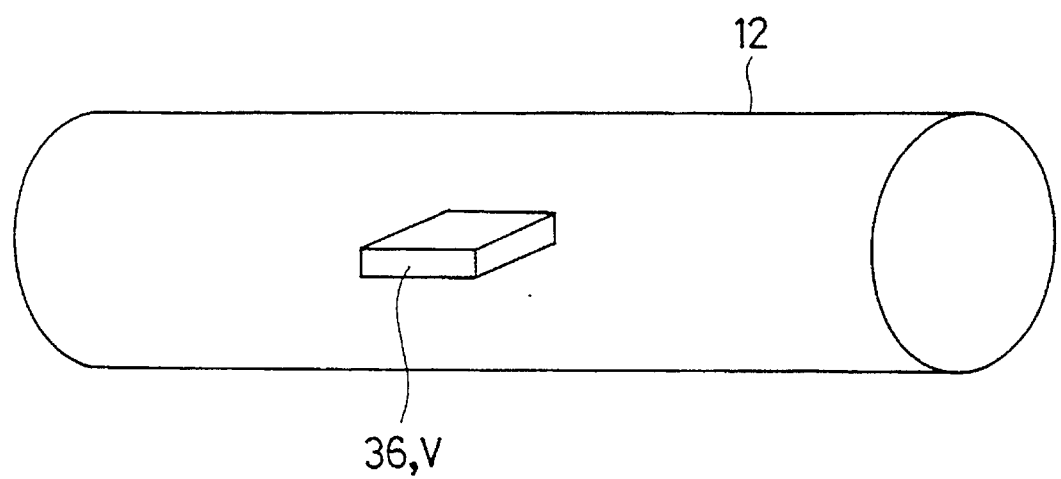
FIG. 7 is a view showing an example of a detection region.

In addition, both in FIGS. 6 and 7, the magnification may be too large to allow the whole volume of the region V for detection to be accommodated within the capturing screen. In such case, the whole screen may be regarded as a magnification image of the detection region V. The actual size of the width W and the length L of the region W is determined by dividing the horizontal width and vertical width of the screen by the magnification of the capturing system. The thickness T of the region W is identical to the thickness of the real image 36 of the plate 28.

Incidentally, in embodiment shown in FIG. 5, the detection region V is generated by forming the real image 36 of the plate 28 inside of living bodies. The region V same as shown in FIG. 5 can be formed by applying laser light to living bodies from different directions via a conversion lens and a scanning means to form a focus (common focus) with a certain depth in living bodies.

In any case, light can be applied to a region having a certain depth in living bodies, so the effect of scattered light is extremely small from other portions of living bodies, for example, portions deeper than a position where blood vessels to be measured are located.

Embodiment 3

Figure 18:
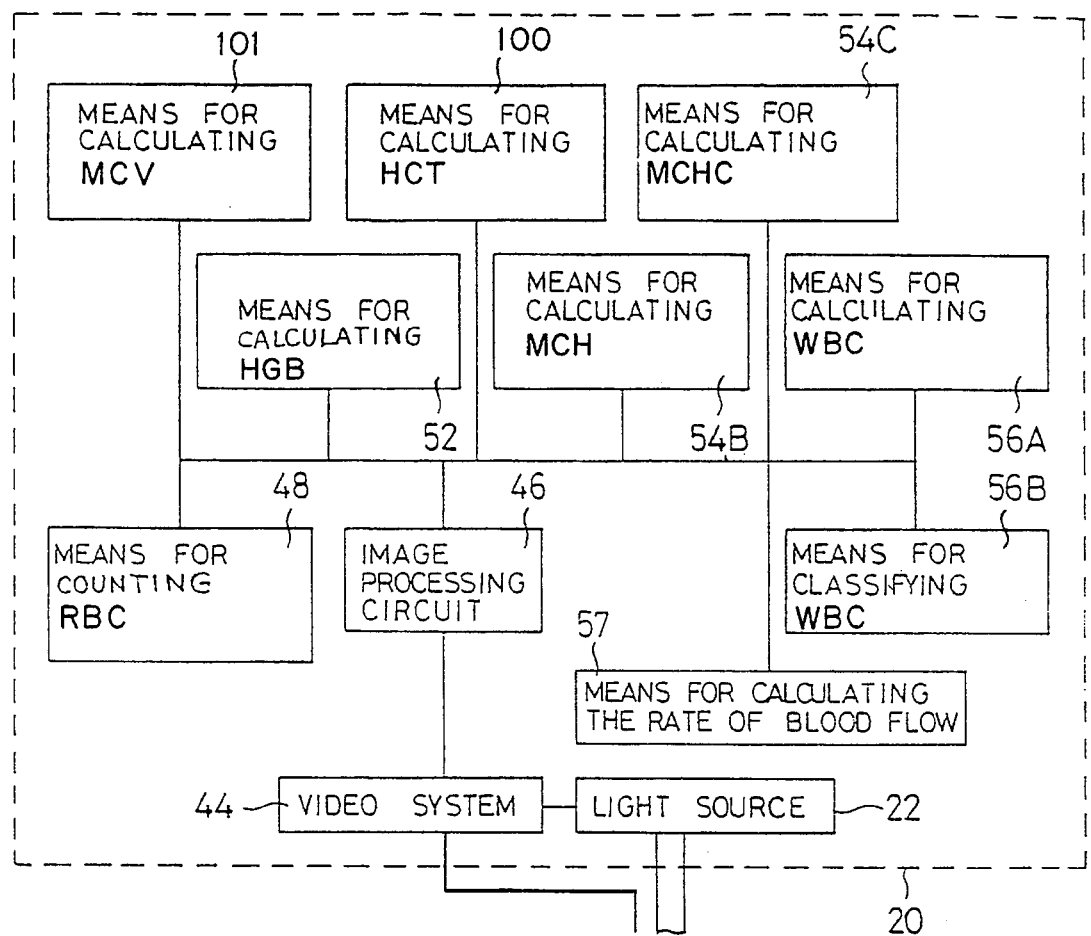
FIG. 18 is a view showing a construction of embodiment 3 of the present invention.

FIG. 18 is a view showing a structure of embodiment 3 of the present invention. The structure shown in FIG. 18 is formed such that the hematocrit calculation means 54A and the mean corpuscular volume calculating means 50 in the structure shown in FIG. 1 is replaced by means 100 for calculating hematocrit value and means 101 for calculating the mean corpuscular volume. Other portions are the same as the structure shown in FIG. 1.

The means 100 for calculating the hematocrit value in this embodiment will be explained.

Figure 19:
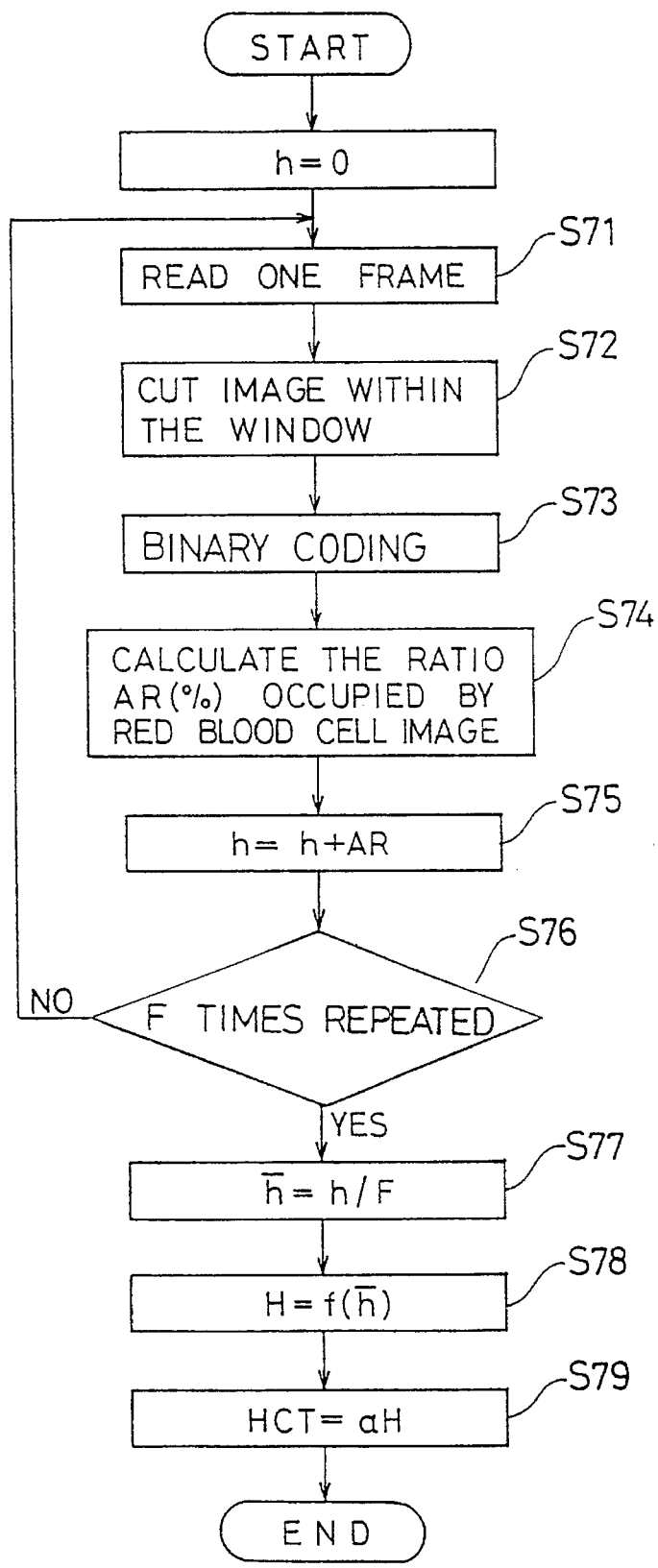
FIG. 19 is a flowchart showing a procedure of calculating hematocrit value of the embodiment shown in FIG. 18.

The means 100 for calculating the hematocrit value calculates a hematocrit value (HCT) from a ratio of the area occupied by the image of red blood cells to a predetermined area of the image captured by the video system 44 and processed by the image processing circuit 46. The procedure for the calculation of the value is shown in the flowchart of FIG. 19. In FIG. 19, the procedure involves reading a frame of an image of the region V one by one from the video system 44 as shown in FIG. 19 (step S71), cutting the read image with a window having a predetermined size (step S72), thresholding the image of the red blood cells within the window with an appropriate value (step S73), determining the ratio AR (%) of the area occupied by the red blood cell image to the area of the window (step S74). This operation is repeated by the predetermined number F of frames (step S76) to determine the cumulative sum h plus AR which is provided in each operation (step S75) thereby calculating the mean value_by dividing h by F (step S77), and determining H by using a function g (which has been theoretically and experimentally determined) for correcting the overlap of the red blood cells (step S78). The H thus given is multiplied by a correction constant a to determine a hematocrit value HCT corresponding to the medium and large size arteries and veins out of data on arterioles and veinlets (step S79).

Then, the means 101 for calculating the mean corpuscular volume will be explained hereinafter. The means 101 operates the following equation to determine the mean corpuscular volume (MCV).

$$MCV=(HCT)/(RBC) \tag{e}$$

where HCT represents a value determined by the hematocrit value means 100, and RBC represents a value determined by the means 48 for calculating the number of the red blood cells.

The means 54A for calculating the hematocrit value as shown in FIG. 1 calculates the hematocrit value (HCT) from the mean corpuscular volume (MCV) and the number of red blood cells. In this case, the calculation time is relatively long because each erythrocyte is recognized and the configuration thereof has to be analyzed in order to determine MCV. However, the hematocrit value calculation means 100 in the embodiment shown in FIG. 18 is not required to recognize each erythrocyte and can obtain HCT directly from images. Thus the calculation time is extremely shortened. Besides, when the calculation time is shortened, the analysis of various screens can be made possible with the result that the accuracy in the calculation of HCT is improved.

Embodiment 4

Figure 20:
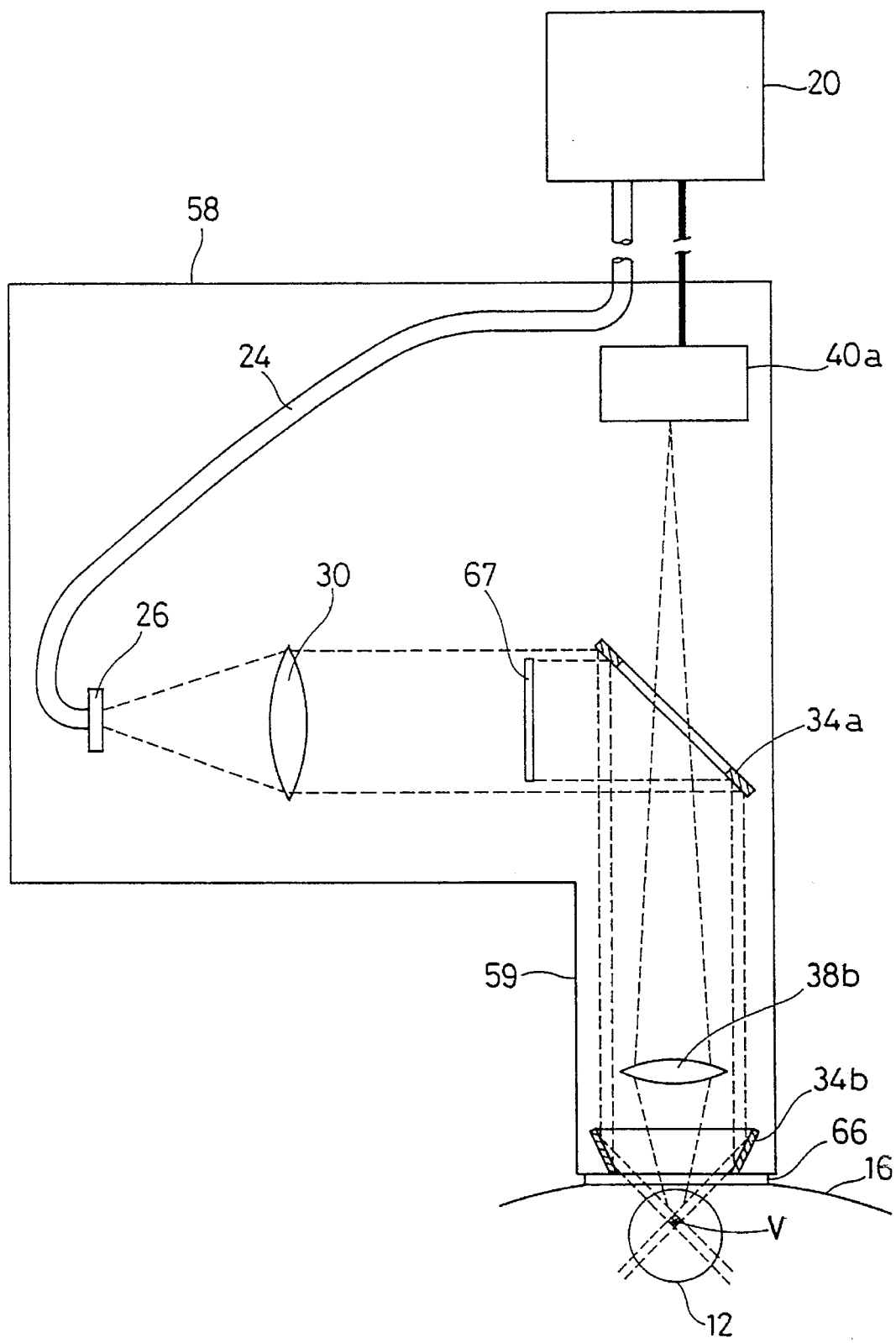
FIG. 20 is a view showing a structure of embodiment 4 of the present invention.

FIG. 20 is a view showing a structure of embodiment 4 of the present invention. Like numerals designate like elements in FIG. 1. Referring to FIG. 20, light generated by the light source in the main body in the analyzer 20 is led into the probe 58 through the optical fiber 24 to irradiate the diffuser 26. Light is diffused by the diffuser 26 and converted into collimated light by the collimator lens 30.

The central portion of the collimated light is shielded by a disk-like shield 67, whereas the periphery of the collimated light is directed to the outside from the tip 59 of the probe 58 via ring-like mirrors 34a and 34b. Light directed to the outside from the tip 59 of the probe 58 irradiates the detection region V in the blood vessel 12 via the transparent plate 66 and the skin surface 16. The light reflected from the detection region V is received by the CCD 40a via the transparent plate 66 and an object lens 38b. The main body of the analyzer 20 analyzes an image captured by the CCD 40a. The main body of the analyzer 20 has been already explained in Embodiment 1 and no further detailed explanation thereof is given here:

The non-invasive blood analyzer according to this embodiment is characterized by irradiating the detection region with a dark field illumination so as to improve the contrast of an image that is captured.

The dark field illumination defined here refers to an illumination mode by which illumination light is directed to the detection region from the outside of the object lens 38b. In other words, the illumination light illuminates the detection region V at an angle $\phi_1$ or $\phi_2$ larger than an angular aperture q of the object lens 38b with respect to the detection region V. Consequently, since the illumination light reflected at the skin surface 16 is directed to the outside of the object lens 38b failing to reach the CCD 40a, the contrast of the image captured by the CCD 40a is greatly improved.

FIG. 21 is a view showing a state in which the probe 58 shown in FIG. 20 and part of the subject (finger nail wall) are relatively fixed. An L-shaped support base 71 is attached to the probe 58. The tip 59 of the probe 58 provides a cylinder 59a extending from the probe 58, and a sliding cylinder 59b attached on the external circumference of the end of the cylinder 59a. The sliding cylinder 59b can slide in the directions of arrows a and b. The transparent plate 66 is fixed to the end of the sliding cylinder 59b.

Springs 72a, 72b are provided on the end of the cylinder 59a that energize the sliding cylinder 59b in the direction of the arrow b. An internal cylinder 73a incorporates the object lens 38b and the ring-like mirror 34b and is fixed to the probe 58 via a micro-motion element 74. Here, the support base 71, the cylinder 59a, the sliding cylinder 59b, the springs 72a, 72b and the transparent plate 66 constitute fixing means, while the sliding cylinder 59b, the springs 72a, 72b and the transparent plate 66 constitute stabilizing means.

When a finger 75 of the subject is inserted between the support base 71 and the transparent plate 66 as shown in FIG. 21, the springs 72a, 72b press the transparent plate 66 on the nail wall of the finger 75 at an appropriate pressure. The detection region V in the blood vessel of the nail wall is fixed in the sight of the CCD 40a thereby preventing a shift motion of the detection region V caused by the fine vibration of the finger 75.

In addition, the focus of the CCD 40a is adjusted by moving the lens 38b in the direction of the optical axis (in the direction shown by arrow a or b) with the micro-motion element 74. As the micro-motion element 74, for example, an element with a piezo element P-720/P-721 (manufactured by Physik Instrument), or an element with an ultrasonic motor can be used.

The transparent plate 66 is detachably attached on the tip 59b of the probe 58 so that the plate 66 can be replaced for each subject. The transparent plate 66 can be replaced for hygienic masons, i.e., for protecting subjects from contracting diseases.

As the transparent plate 66, a glass plate with a resin-made flexible film can be used.

Otherwise, the transparent plate 66 itself is not replaced, and a replaceable film can be closely contacted to the finger 75.

Figure 22:
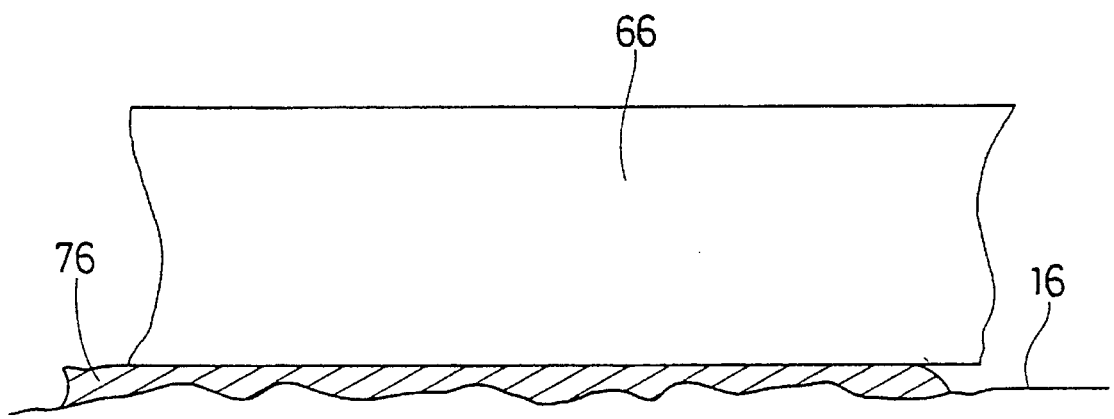
FIG. 22 is a view illustrating an essential part of FIG. 21.
Figure 23:
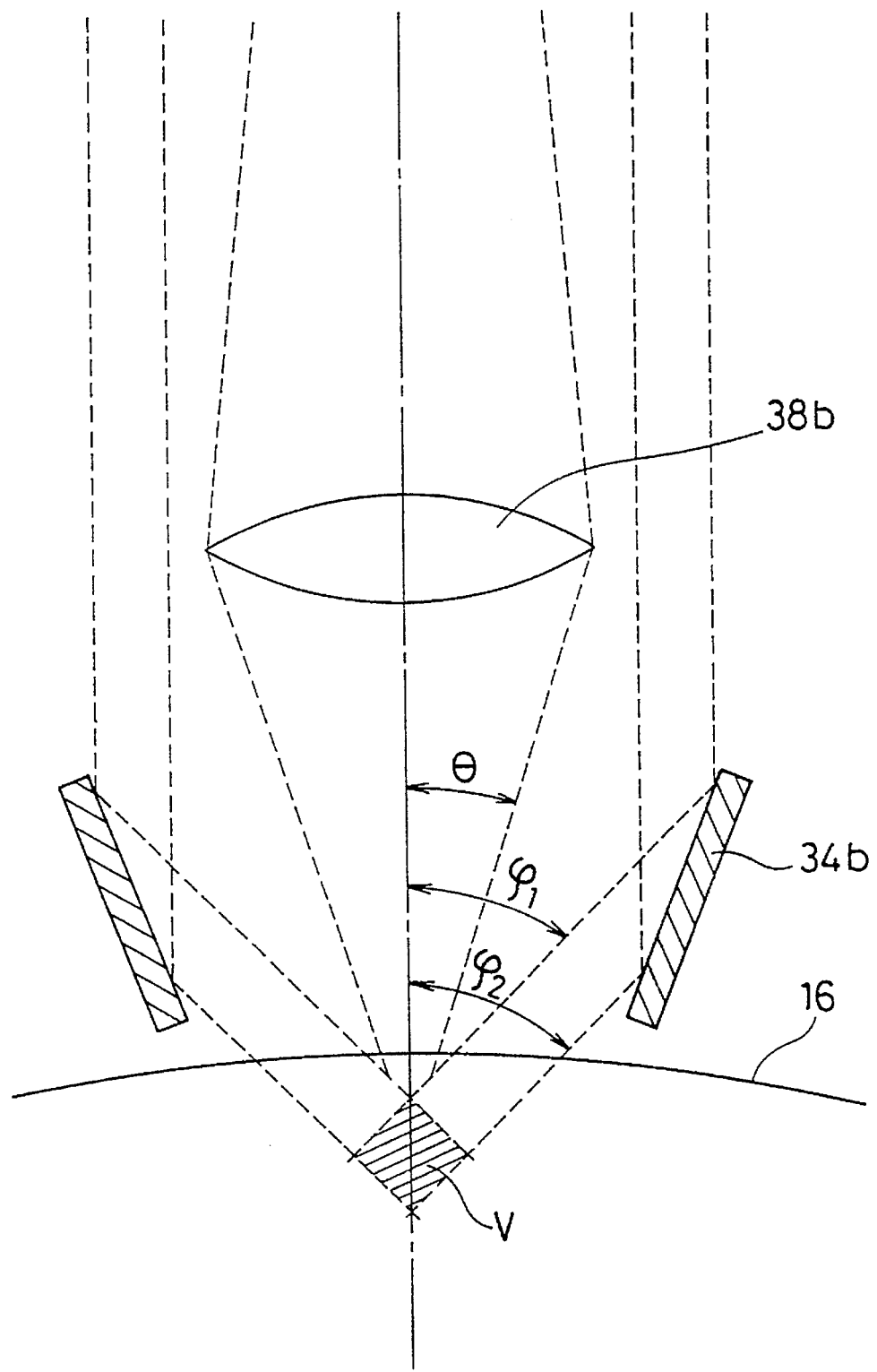
FIG. 23 is a partial expanded view of FIG. 21.

Furthermore, as shown in FIG. 22 a liquid or gelatinous optical medium safe for the living body is more preferably intervened between the skin surface 16 and the transparent plate 66 in order to prevent the illumination light from irregularly reflecting on the skin surface 16 and obtain a sharp image of the detection region V.

As the light medium 76, oil or cream can be used. In embodiment 4, as the plate 66 contacting the living body, a transparent plate is used. Instead of plate 66, however, an opague plate with a hole transmitting light can be used since the opague plate can prevent the shift of the detection region.

Therefore, the present invention enables non-invasively capturing an image of a predetermined volume of blood passing through the blood vessel and counting the number of blood cells per unit volume by analyzing the image thereof thereby calculating the hematocrit value, hemoglobin and corpuscular constant. Furthermore, it is possible to classify white blood cells because the image is clear despite the fact that they are non-invasively captured.

What is claimed is:

1. A non-invasive blood analyzer comprising:

light application means for applying light to a detection region in a blood vessel contained in a part of a living body and having blood flowing therethrough in a given direction;

imaging means, responsive to light reflected from said detection region, for capturing an image of the detection region from the reflected light, wherein the light applied to the detection region and the light reflected from the detection region travel in nearly mutually exclusive paths;

stabilizing means for stabilizing a focus of said imaging means with respect to the detection region; and analysis means for analyzing characteristics of blood cells contained in the detection region by processing images captured with said imaging means.

2. A non-invasive blood analyzer according to claim 1 wherein said stabilizing means includes a transparent member which is adapted to contact the part of the living body and said imaging means images the detection region through said transparent member.

3. A non-invasive blood analyzer according to claim 2 wherein said transparent member is either a plate or a flexible film which transmits light.

4. A non-invasive blood analyzer according to claim 2 wherein said stabilizing means further provides a liquid or gelatinous optical medium that intervenes between said transparent member and the part of the living body.

5. A non-invasive blood analyzer according to claim 1 wherein said imaging means further provides adjusting means for adjusting the focus with respect to the detection region.

6. A non-invasive blood analyzer according to claim 1 wherein said imaging means provides an object lens which collects light from the detection region, and said light application means applies light to the detection region at an angle larger than an angular aperture of the object lens.

7. A non-invasive blood analyzer according to claim 1 wherein said imaging means comprises an optical system for channeling reflected light from said detection region, an imaging sensor for receiving the channelled light to capture the image and image recording means for recording the captured image of said imaging sensor.

8. The non-invasive blood analyzer of claim 7, wherein the image recording means records the captured image in a memory.

9. A non-invasive blood analyzer according to claim 1 wherein the detection region includes a volume region in which an image of each blood cell is optically differentiated by said imaging means.

10. A non-invasive blood analyzer according to claim 1 wherein the detection region is a region defined by two parallel planes and further where said light application means applies the light orthogonally or diagonally relative to the direction of blood flow existing in said blood vessel.

11. A non-invasive blood analyzer according to claim 1 wherein said light application means applies light to said detection region in one direction and said imaging means collects light from said detection region in a direction non-parallel to the light application direction.

12. A non-invasive blood analyzer according to claim 1 wherein said light application means and said imaging means are constituted so that said detection region is repeatedly imaged at a predetermined time interval.

13. A non-invasive blood analyzer according to claim 1 wherein said imaging means includes a polarizing means for removing scattered light reflected from said detection region.

14. A non-invasive blood analyzer according to claim 1 wherein said light application means provides polarizing means for applying polarizing light to the detection region.

15. A non-invasive blood analyzer according to claim 1 wherein said blood cells include red and white blood cells and said analysis means analyzes the number of red blood cells and/or white blood cells therein.

16. A non-invasive blood analyzer according to claim 1 wherein said analysis means calculates a hematocrit.

17. A non-invasive blood analyzer according to claim 1 wherein said analysis means comprises a light intensity analysis means for analyzing a light intensity of the light reflected from said detection region thereby calculating a hemoglobin value.

18. A non-invasive blood analyzer according to claim 1 wherein said blood cells include red blood cells and said analysis means identifies the red blood cells and calculates a mean corpuscular volume by determining an area of each red blood cell from the image and multiplying a mean value of the area by a predetermined constant.

19. A non-invasive blood analyzer according to claim 1 wherein said blood vessel comprises arteriolas, veinlets, or capillary vessels and said analysis means translates blood cell information obtained from arteriolas and veinlets or capillary vessels into blood cell information corresponding to medium-size and large arteries or veins.

20. A non-invasive blood analyzer according to claim 1, wherein said blood cells include red blood cells and said captured image is of a predetermined area; and wherein said analysis means includes means for calculating a hematocrit value from a ratio of an area occupied by the red blood cells imaged within said predetermined area, to said predetermined area of said image.

21. A non-invasive blood analyzer according to claim 1 wherein said blood cells include red blood cells and said analysis means comprises means for calculating a hematocrit value and the number of red blood cells and obtaining a mean corpuscular volume by dividing the hematocrit value by the number of red blood cells.

22. The non-invasive blood analyzer of claim 1, wherein a captured surface of the detection region and a capturing surface of the imaging means are disposed so as to enable swing and tilt photography.

23. The non-invasive blood analyzer of claim 1, further comprising:

fixing means for relatively fixing said imaging means and the part of the living body.

24. The non-invasive blood analyzer of claim 1, wherein said light application means and said imaging means form one image with the light application and imaging process during an interval of one ten thousandth to one billionth of a second.

25. The non-invasive blood analyzer of claim 24, wherein the interval ranges from one fifty-thousandth to one two-hundred thousandth of a second.

26. The non-invasive blood analyzer of claim 25, wherein the light application means is an intermittent light source and the imaging means is a CCD image sensor.

27. A non-invasive blood analyzer according to claim 1, wherein said analysis means calculates a hemoglobin value.

28. A non-invasive blood analyzer according to claim 1, wherein said analysis means calculates a mean corpuscular volume.

29. A non-invasive method for analyzing blood comprising the steps of:

relatively fixing an imaging device and a part of a living body to stabilize a focus of the imaging device with respect to a detection region in the part;

applying light along a first path to the detection region in a blood vessel contained in said part;

imaging the detection region from light reflected from the detection region along a second path nearly exclusive of the first path, thereby forming an image of the detection region; and processing the formed image to analyze a number of blood cells contained in said detection region.

30. A non-invasive method according to claim 29 wherein the steps of stabilizing the focus and imaging the detection region further comprise bringing a light-pervious member into contact with the part of the living body and imaging the detection region through the light-pervious member, respectively.

31. The non-invasive method of claim 29, wherein the light application and imaging steps are performed during an interval of one ten thousandth to one billionth of a second to form one image.

32. The non-invasive method of claim 31, wherein the interval ranges from one fifty-thousandth to one two-hundred thousandth of a second.

33. A non-invasive blood analyzer comprising:

light application means for applying light toward a region of a blood vessel contained in a part of a living body;

light blocking means for blocking a first portion of the applied light, a second portion of the applied light travelling to the region along a first path;

imaging means for receiving the second portion of the applied light, subsequent to reflection from the region and travel along a second path nearly exclusive of the first path, and for capturing an image of the region;

stabilizing means for stabilizing a focus of the imaging means with respect to the region; and analysis means for analyzing characteristics of blood cells contained in the region by processing the captured image.

34. The non-invasive blood analyzer of claim 33, wherein the light blocking means is a light blocking disk.

35. A non-invasive method for analyzing blood comprising the steps of:

applying light toward a region of a blood vessel contained in the living body;

blocking a first portion of the applied light, a second portion of the applied light travelling to the region along a first path;

stabilizing a focus of an imaging device with respect to the region;

imaging the detection region in the imaging device, upon receipt of the second portion of the applied light subsequent to reflection from the region and travel along a second path nearly exclusive of the first path, to form an image of the detection region; and processing the formed image to analyze characteristics of blood cells contained in the detection region.

* * * * *